United States Patent [19]
Uhlmann et al.

[11] Patent Number: 6,028,182
[45] Date of Patent: *Feb. 22, 2000

[54] METHYLPHOSPHONIC ACID ESTERS, PROCESSES FOR THEIR PREPARATION, AND THEIR USE

[75] Inventors: Eugen Uhlmann, Glashütten; Chris Meier, Bad Homburg, both of Germany

[73] Assignee: Hoechst Aktiengesellschaft, Frankfurt am Main, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/578,686

[22] PCT Filed: Jun. 29, 1994

[86] PCT No.: PCT/EP94/02121

§ 371 Date: Jan. 2, 1996

§ 102(e) Date: Jan. 2, 1996

[87] PCT Pub. No.: WO95/01363

PCT Pub. Date: Jan. 12, 1995

[30] Foreign Application Priority Data

Jul. 1, 1993 [DE] Germany .............................. 43 21 946

[51] Int. Cl.$^7$ .............................. C12Q 1/68; C07H 19/00; C07H 21/00; C07H 21/02
[52] U.S. Cl. ........................... 536/22.1; 435/6; 536/23.1; 536/24.5; 536/25.3; 536/25.33
[58] Field of Search ................................ 435/6; 536/22.1, 536/23.1, 24.5, 25.3, 25.33

[56] References Cited

FOREIGN PATENT DOCUMENTS

PCT/WO93/
10140 5/1993 WIPO .

OTHER PUBLICATIONS

Meier, "5', 5'–0–Dinucleoside (alpha–hydroxybenzyl)phosphonates as a lipophilic potential prodrug of ddT," Chemical Abstracts, vol. 120, No. 25, Jun. 20, 1994, pp. 974.

Roelen, "Synthesis of alkylphosphon(othio)ate analogues of DNA," Tetrahedron Letters, vol. 33, 1992, pp. 2357–2360.

Meier, "O–Alkyl–5', 5'–dinucleoside–phosphates as combined prodrugs of antiviral and antibiotic compounds," Bioorganic Med. Chem. Lett., vol. 1, 1991, pp. 527–530.

Chris Meier et al., Lipophilic α–Hydroxybenzylphosphonates as Prodrugs of 3'–Azido–2', 3—dideoxythymidine (AZT), Liesbigs Ann. 1995, 2195–2202.

Chris Meier et al., Homo Dinucleoside–α–Hydroxyphoshonate Diesters as Prodrugs of the Antiviral Nuceloside Analogues 2', 3'–Dideoxythymidine and 3'–Azido–2', 3'–Dideoxythymidine, Nucelosides & Nucelositeda, 14(3–5), 759–762 (1995).

Chris Meier, Lipohilic 5', 5'–0–Dinucleoside–α–hydroxybenzylphophonic Acid Esters as Potential Prodrugs of 2', 3'–Dideoxythymidine (ddT), Agnew. Chemical Int. Ed. Engl 1993, vol. 32, No. 12, pp. 1704–1706.

Yoshino et al. "Organic phosphorus compounds. 2. Synthesis and coronary vasodilator activity of (benzothiazolylbenzyl)phosphonate derivatives." J. Med. Chem. vol. 32, pp. 1528–1532, 1989.

Primary Examiner—Ardin H. Marschel
Assistant Examiner—Jezia Riley
Attorney, Agent, or Firm—Finnegan, Henderson, Farabow, Garrett & Dunner, L.L.P.

[57] ABSTRACT

Methylphosphonic acid esters, processes for their preparation, and their use

From the compounds of the formula I,

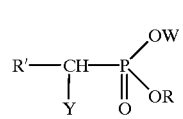

(I)

in which the substituents R', Y, W and R have the meanings mentioned, in vivo have the action of the active compound radical W together with improved pharmacokinetics.

11 Claims, No Drawings

METHYLPHOSPHONIC ACID ESTERS, PROCESSES FOR THEIR PREPARATION, AND THEIR USE

This application claims priority under 35 U.S.C. §371 of prior international application Ser. No. WO/95/01363.

The present invention relates to methylphosphonic acid esters, processes for their preparation, and their use.

Phosphorylated active compound derivatives are already known which have in some cases also been employed for pharmaceutical purposes. Thus, for example, in J. Med. Chem. 1993, 36, 1048–1052 phosphoamidate esters with AZT are described. The antiviral activity of these compounds, however, is less than that of AZT by the factor 10 and the toxicity of the compounds mentioned is higher than that of AZT by the factor 5. In J. Med. Chem. 1991, 34, 1830–1837, phosphotriester derivatives with AZT are described; in these compounds too the activity is lower and the toxicity greater than in the case of AZT. Similar results are obtained with related compounds, which are reported in J. Org. Chem. 1992, 57, 7300–7307.

With the intention of obtaining phosphorylated active compound derivatives which do not have the disadvantages of relevant prior art compounds, it has now been found that the methylphosphonic acid esters according to the invention have outstanding properties. The invention accordingly relates to 1) compounds of the formula I,

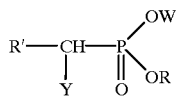
(I)

characterized in that

Y has the meaning of OH, SH, OAc or SAc, where Ac=(C1–C18)-acyl, which is optionally unsaturated 1–3 times, R' is aryl, heteroaryl or alkyl, W has the meaning of a pharmaceutical active compound radical, R has the meaning of W, where R and W can be identical or different, or R is an optionally substituted alkyl radical or W and R, together with the phosphonate radical carrying them, form an oligonucleotide where W is a radical of the formula II and R is a radical of the formula II'

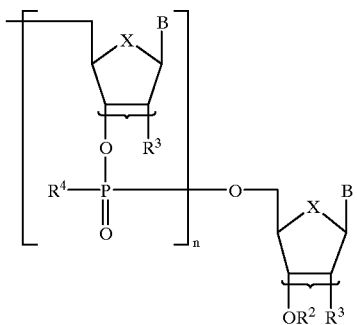
(II)

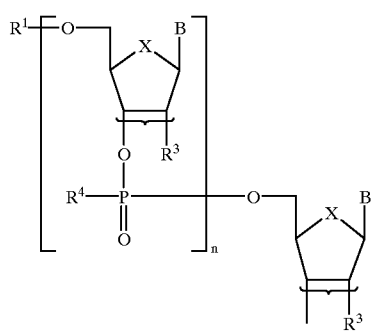
(II')

where X is oxy, sulphanediyl or methylene,

B independently of one another is a nucleotide base, n independently of one another is an integer from 0 to 50, $R^1$ and $R^2$ independently of one another are H (C1–C18) acyl or a radical of the formula

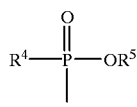

in which $R^4$ is $O^-$, $S^-$, $CH_3$ or CHYR', where R' and Y are as defined above and $R^5$ is an optionally substituted alkyl radical having 1–18 carbon atoms, $R^3$ is independently of one another H, O(C1–C18)-alkyl, O(C1–C18)-acyl, F, Cl, $N_3$, $NH_2$ or $NHR^6$ where $R^6$ is (C1–C6)-alkyl or -acyl and the curved bracket indicates that $R^3$ and the adjacent phosphonyl radical can be in the 2' or 3' position.

2. Preferred compounds of the formula I are as elucidated under 1), characterized in that Y has the meaning of OH, SH, OAc or SAc, where Ac=(C1–C8)-acyl, which is optionally unsaturated 1–3 times, R' is aryl having 6–14 carbon atoms, optionally substituted by up to three radicals which are independent of one another, selected from the group consisting of (C1–C5)-alkyl, halogen, $NO_2$, CN, (C1–C6)-alkoxy, amino, (C1–C4)-alkylamino, (C1–C8)-dialkylamino, where a (C3–C8)-alkylene radical in which a $CH_2$ group can also be replaced by oxy can also be fused onto the aryl radical;

heteroaryl having 3 to 13 carbon atoms and up to 3 heteroatoms selected from the group consisting of N, O and S;

(C1–C16)-alkyl, which is branched or unbranched, saturated or unsaturated 1–3 times, optionally substituted independently of one another by up to three substituents selected from the group consisting of halogen, CN, $NO_2$ and (C1–C3)-alkoxy, W has the meaning of a pharmaceutical active compound radical, R has the meaning of W, where R and W can be identical or different, or R is [lacuna] or (C1–C16)-alkyl, which can be branched or unbranched and is optionally substituted independently of one another by up to 3 radicals from the group consisting of halogen, CN, (C1–C8)-acyloxy, (C1–C18)-alkoxy or W and R, together with the phosphonate radical carrying them, form an oligonucleotide where W is a radical of the formula II and R is a radical of the formula II' where X is oxy or sulphanediyl, B independently of one another is a nucleotide base, n independently of one another is an integer from 0 to 30, $R^1$ and $R^2$ independently of one another are H (C1–C12)-acyl or a radical of the formula

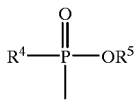

in which $R^4$ is O, S, $CH_3$ or CHYR', where R' and Y are as defined above and $R^5$ is an optionally substituted alkyl radical having 1–12 carbon atoms, $R^3$ independently of one another is H, O(C1–C12)-alkyl, O(C1–C12)-acyl, Cl, $N_3$, $NH_2$ or $NHR^6$ where $R^6$ is (C1–C3)-alkyl or -acyl and the curved bracket indicates that $R^3$ and the adjacent phosphonyl radical can be in the 2' or 3' position, 3) Particularly preferred compounds of the formula I are as elucidated under 1) or 2), characterized in that Y has the meaning of OH, SH, OAc or SAc, where Ac=(C1–C3)-acyl, which is optionally unsaturated 1–3 times, R' is aryl having 6–14 carbon atoms, optionally substituted by up to 3 radicals which are independent of one another, selected from the group consisting of (C1–C3)-alkyl, F, Cl, $NO_2$, CN, (C1–C4)-alkoxy, amino, (C1–C3)-alkylamino, (C1–C6)-dialkylamino, where a (C3–C8)-alkylene radical in which a $CH_2$ group can also be replaced by oxy can also be fused onto the aryl radical;

heteroaryl having 3 to 6 carbon atoms and up to 3 heteroatoms selected from the group consisting of N, O and S;

(C1–C8)-alkyl, which is branched or unbranched, saturated or unsaturated 1–3 times, optionally substituted independently of one another by up to three substituents selected from the group consisting of Cl, CN, $NO_2$ and (C1–C3)-alkoxy, W has the meaning of a 5'-, 3' or 2' nucleoside analogue, of a steroid, of a sugar, of an inositol or of a peptide having at least one amino acid Ser or Tyr and a total of up to 20 natural amino acids, R has the meaning of W or is (C1–C8)-alkyl, which can be branched or unbranched and is optionally substituted by up to 2 radicals from the group consisting of halogen, CN, (C3–C6)-acyloxy, (C8–C18)-alkoxy or W and R, together with the phosphonate radical carrying them, form an oligonucleotide where W is a radical of the formula II and R is a radical of the formula II' where X is oxy, B independently of one another is a nucleotide base, n independently of one another is an integer from 0 to 20, $R^1$ and $R^2$ independently of one another are H (C1–C8)-acyl or a radical of the formula

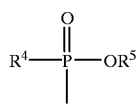

in which $R^4$ is O, S, $CH_3$ or CHYR', where R' and Y are as defined above and $R^5$ is an optionally substituted alkyl radical having 1–8 carbon atoms, $R^3$ independently of one another is H, O(C1–C8)-alkyl, O(C1–C8)-acyl, Cl or $N_3$, and the curved bracket indicates that $R^3$ and the adjacent phosphonyl radical can be in the 2' or 3' position.

4) Very particularly preferred compounds of the formula are as elucidated above under 1) to 3), characterized in that Y has the meaning of OH, R' is aryl having 6 carbon atoms, optionally substituted by up to 3 radicals which are independent of one another, selected from the group consisting of (C1–C3)-alkyl, F, Cl, $NO_2$, CN, (C1–C4)-alkoxy, amino, (C1–C3)-alkylamino, (C1–C6)-dialkylamino, where a (C3–C6)-alkylene radical in which a $CH_2$ group can also be replaced by oxy can also be fused onto the aryl radical;

heteroaryl having 3 to 6 carbon atoms and up to 3 heteroatoms selected from the group consisting of N, O and S;

(C1–C8)-alkyl, which is branched or unbranched, saturated or unsaturated 1–3 times, preferably unsaturated in conjugated form having an unsaturated bond in the alpha-position, optionally substituted independently of one another by up to three substituents selected from the group consisting of Cl, CN, $NO_2$ and (C1–C3)-alkoxy, W has the meaning of a 5'- or 3' nucleoside analogue, R has the meaning of W or is (C1–C4)-alkyl, which can be branched or unbranched or W and R, together with the phosphonate radical carrying them, form an oligonucleotide where W is a radical of the formula II and R is a radical of the formula II' where X is oxy, B independently of one another is a nucleotide base, n independently of one another is an integer from 0 to 15, $R^1$ and $R^2$ independently of one another are H (C1–C4)-acyl or a radical of the formula

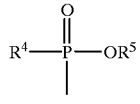

in which $R^4$ is O, S, $CH_2$ or CHYR', where R' and Y are as defined above and $R^5$ is an optionally substituted alkyl radical having 1–3 carbon atoms, $R^3$ independently of one another is H, O(C1–C3)-alkyl, O(C1–C3)-acyl, Cl or $N_3$, and the curved bracket indicates that $R^3$ and the adjacent phosphonyl radical can be in the 2' or 3' position.

5) Compounds of the formula I which are furthermore of particular importance are as elucidated under 1) to 4), characterized in that Y has the meaning of OH, W has the meaning of a 5'- or 3' nucleoside analogue, R has the meaning of W or is (C1–C4)-alkyl, which can be branched or unbranched, R' is aryl having 6 carbon atoms, optionally substituted by up to 3 radicals which are independent of one another, selected from the group consisting of Cl, $NO_2$, CN, (C1–C3)-alkoxy, amino and (C1–C3)-alkylamino.

The term "independently of one another" used above in connection with substituents which occur several times (e.g. "B") is intended to make it clear that in one compound in each case the particular substituents can be different, which also applies to elements repeating themselves n times.

Examples of acyl groups mentioned in the preceding definitions are acetyl, butyryl, pivaloyl, crotonoyl, pentanoyl, hexanoyl, octadecanoyl or oleyl.

Suitable alkyl groups are, for example, methyl, ethyl, propyl, butyl, isobutyl, pentyl or hexyl.

Exemplary aryl groups are phenyl or naphthyl.

Suitable heteroaryl groups are, for example, pyridyl, oxazole, furyl, benzofuryl or phenothiazinyl.

Exemplary alkylamino groups are the methyl and the dimethylamino groups.

Exemplary dialkylamino groups are the dimethylamino and the diethylamino group.

Nucleoside analogues which are particularly suitable according to the invention are compounds derived from the bases adenine, cytosine, guanine, thymine, purine, 7-deazaadenine, 7-deazaguanine or 5-chlorocytosine, in particular, for example, 3'-deoxy-3'-azidothymidine, 2',3'-dideoxy-2',3'-didehydrothymidine, 2',3'-dideoxythymidine, 2',3'-dideoxyuridine, 2',3'-dideoxyadenosine, 2',3'-dideoxyinosine, 3'F,3'-deoxythymidine, acyclovir and gancyclovir.

The abovementioned radicals $R^5$ can optionally be substituted by halogen, preferably Cl, $CF_3$, CN, $NH_2$ or (C1–C6)- preferably (C1–C3)-alkoxy.

The present invention furthermore relates to a process for the preparation of compounds according to one or more of claims 1-5 which is characterized in that a) a compound of the formula III is reacted with a compound of the formula IV,

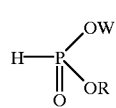

(III)

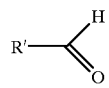

(IV)

or in that b) a compound of the formula V is reacted with compounds of the formula VI in any desired sequence and using a condensing agent, or in that c) a compound of the formula V is reacted with compounds of the formula VI and of the formula VII in any desired sequence and using a condensing agent,

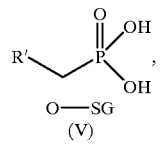

(V)    WOH,    ROH
       (VI)    (VII)

where SG is a protective group which is optionally removed to obtain the compound of the formula I, or a nucleotide unit having a 3' (2')-terminal H-phosphonate group and protected 5'-hydroxy group is reacted with a further nucleotide unit having a free 5'-hydroxy group and protected 3'(2')-hydroxy group in the presence of an activating agent to give the H-phosphosphonate dinucleoside and this is condensed with an aldehyde to give the dinucleoside α-hydroxyalkyl(aryl) phosphonate, which after reaction to give its activated derivatives reacts with further (oligo)nucleotide fragments to give oligonucleotides, temporarily introduced protective groups being removed, or in that a) a nucleotide unit having a 3'(2')-terminal phosphorus (III) or phosphorus(V) group is reacted with a free 5'-hydroxy group of a further nucleotide unit or growing oligonucleotide chain in the presence of a condensing agent or b) its activated derivatives, or the oligonucleotide analogue is built up in fragments in the same way, protective groups temporarily introduced into the oligonucleotides obtained according to a) or b) for the protection of other functions are removed and the oligonucleotide analogues of the formula I thus obtained in which W is a radical of the formula II and R is a radical of the formula II' are optionally converted into their physiologically tolerable salt.

The reaction described under a) preferably proceeds under the following conditions.

A) Reaction of the phosphonate diester of the formula III with the appropriate substituted aldehydes of the formula IV in an organic solvent, e.g. in dry triethylamine ($NEt_3$) at elevated temperature, preferably at boiling heat.

B) Reaction of the phosphonate diester of the formula III with the aldehyde of the formula IV in a dry aprotic solvent, e.g. tetrahydrofuran (THF) with addition of an organic base, e.g. $NEt_3$ or quinine at room temperature ±10° C.

After reaction is complete, the products are purified by known methods, e.g. by chromatography.

The reactions described in b) and c) proceed under conditions known for esterifications in the prior art. Particularly good results are achieved by means of intermediate active ester formation, for example with triazole/dimesitylenesulphonyl chloride.

Suitable protective groups which are optionally removed after the reaction according to methods of the prior art are, for example, alkylsilyl, alkylarylsilyl and acyl, in particular t-butyldimethylsilyl. The last-mentioned protective group can advantageously be removed using ammonium fluoride in methanol.

The compounds according to the invention can also be prepared stereoselectively according to various methods of the prior art. A preferred starting point for the introduction of the chirality on the α-carbon atom is the reaction of the C anion of a t-butyldimethylsilyl-protected alcohol (compound of the formula V) with the oxazaphospholidine derived from (+)-ephedrine as a chiral auxiliary. The oxazaphospholidine is obtained, for example, by reaction of phosphoryl chloride with (+)-ephedrine in 60% yield and a diastereomer ratio of 24:1. A further possibility for the introduction of the chirality consists in the enantioselective oxazaborolidine-catalysed reduction (Tetrahedron Lett., 31, 611, (1990).

The starting substances needed for carrying out the above-mentioned reactions are commercially available, or can be prepared according to generally known procedures. Some preferred preparation methods are described in the examples.

The nucleoside H-phosphonate diesters of the formula (III), which are used as starting compounds, can be prepared, for example, by the reaction of diisopropylaminedichlorophosphine with the corresponding nucleosides to give the phosphoramidite, which can be hydrolysed directly with tetrazole activation using water in a "one-pot reaction" to give the compounds of the formula III.

Alternatively, the synthesis takes place, for example, by the esterification of a 5'-nucleoside phosphorous acid monoester with a second equivalent of the nucleoside with pivaloyl chloride activation. A 5'-nucleoside phosphorous acid monoester is accessible by reaction of phosphorus trichloride with imidazole to give the phosphorus triimidazolide, after reaction with the corresponding nucleoside and subsequent hydrolysis.

Alternatively, the compounds of the formula III can be prepared by the esterification of a 5'-nucleoside phosphorous acid monoester with a second equivalent of the appropriate nucleoside with pivaloyl chloride activation.

The preparation of the compounds of the formula I having a radical of the formula II and II' is preferably carried out such that in principle dimeric nucleotides of the formula XI as described above are prepared, which are then incorporated into oligonucleotides by customary methods. For example (Scheme 1), a 5'-protected nucleoside 3'-H-phosphonate ester of the formula VIII can be reacted with a 3'-protected 5'-hydroxy component of the formula IX in the presence of a condensing agent such as pivaloyl chloride in pyridine to give the dinucleoside H-phosphonate ester of the formula X. This is then reacted with the appropriate aldehyde to give the dinucleoside hydroxyalkylphosphonate. The free α-hydroxy group must be protected for further reactions, preferably using the TBDMS (t-butyldimethylsilyl) protective group, which is removed at the end of the synthesis using fluoride ions. Formula XI compounds are reacted, for example after removal of the 3'-protective group ($SG^2$), to give the phosphoramidite of the formula XII, which can be introduced into oligonucleotides as analogues of the phosphoramidites according to known methods.

The prodrug nucleotides, however, can also be built up as monomeric units by condensation of appropriately protected nucleoside-3' (or 5')-phosphonate esters with the 5' (or 3'-)-hydroxy group of a 3' (or 5') protected nucleoside (Scheme 2). Preferably, the nucleoside-3'-phosphonamidates of the formula XIII (where (P)=P-N (ipropyl)$_2$) are used, which can be incorporated into oligonucleotides according to customary methods.

Oligonucleotide analogues of the formula I having a radical of the formula II or II' are prepared, similarly to the synthesis of biological oligonucleotides, in solution or preferably on solid phase, if appropriate with the aid of an automatic synthesis apparatus.

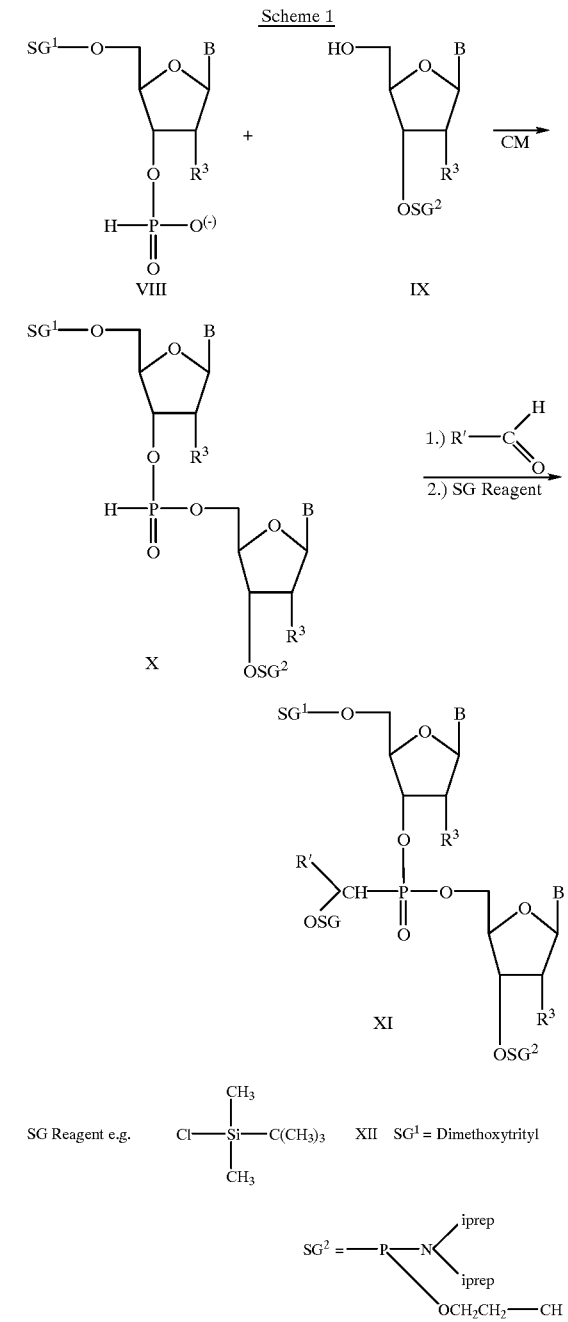

Scheme 1

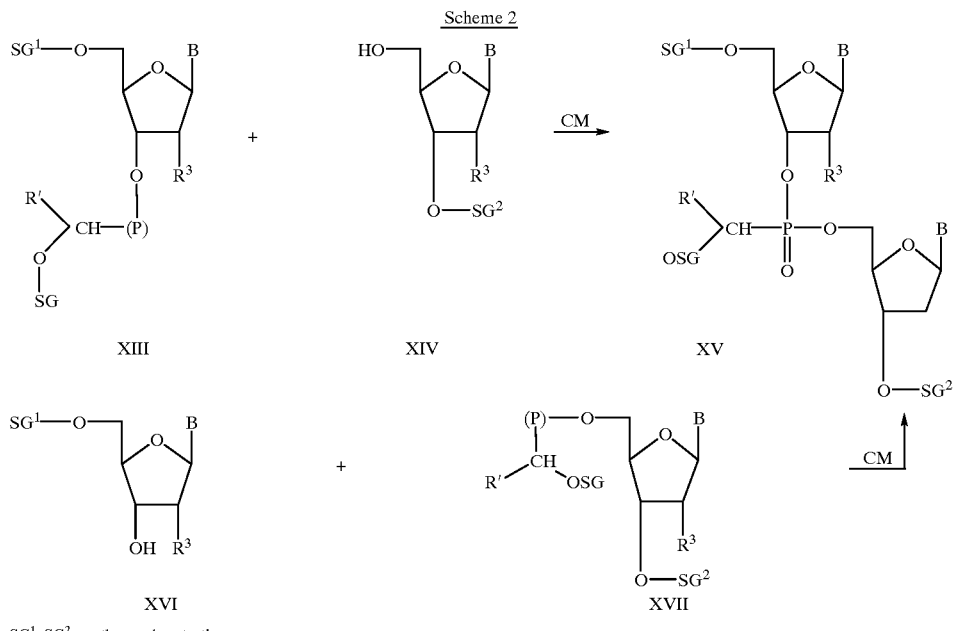

Scheme 2

SG¹, SG² = orthogonal protective groups e.g. SG¹ = Dimethoxytrityl

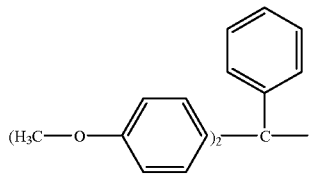

e.g. SG² = Levulinoyl

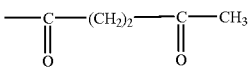

CM = Condensing agent

I (P) = 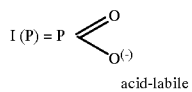

acid-labile

II (P) = 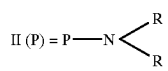

The compounds of the formula I according to the invention and their pharmaceutically tolerable salts exhibit the pharmaceutical activity of the active compounds on which they are based. Since they additionally exhibit favourable toxicological and pharmacokinetic properties, they are useful chemotherapeutics.

The invention thus also relates to pharmaceuticals, in particular pharmaceuticals for the control of virus disorders, which are characterized in that they contain one or more of the compounds according to the invention. They can be administered, for example, orally, intramuscularly or intravenously.

Pharmaceuticals which contain one or more compounds of the general formula I as active compound can be prepared by mixing the compounds of the formula I with one or more pharmacologically tolerable excipients or diluents, such as, for example, buffer substances, and bringing them into a suitable preparation form.

Diluents which may be mentioned are, for example, polyglycols, ethanol and water. Buffer substances are, for example, organic compounds, such as N',N'-dibenzylethylenediamine, diethanolamine, ethylenediamine, N-methylglucamine, N-benzylphenethylamine, diethylamine, tris(hydroxymethyl)aminomethane, or inorganic compounds, such as phosphate buffer, sodium bicarbonate, sodium carbonate. For oral administration, suspensions or solutions in water with or without buffer substances are preferably suitable. It is also possible to administer the active compounds as such without excipients or diluents in a suitable form, for example in capsules.

Suitable doses of the compounds of formula I or their pharmaceutically tolerable salts are highly dependent on the respective active compounds on which they are based; e.g. in the case of AZT they are approximately 0.4 g, preferably 0.5 g to at most 20 g per day for an adult of approximately 75 kg body weight. Individual or, in general, multiple doses can be administered, where the individual dose can contain the active compound in an amount from approximately 50 is 1000 mg.

The present invention furthermore relates to the use of the novel oligonucleotide analogues (compounds of the formula I having a radical of the formula II and II' as inhibitors of gene expression (anti-sense oligonucleotides, ribozymes, sense oligonucleotides and triplex forming oligonucleotides).

Oligonucleotides are used to a growing extent as inhibitors of gene expression (G. Zon, Pharmaceutical Research 5, 539 (1988); J. S. Cohen, Topics in Molecular and Structural Biology 12 (1989) Macmillan Press; C. Helene and J. J. Toulme, Biochemica and Biophysica Acta 1049, 99 (1990); E. Uhlmann and A. Peyman, Chemical Reviews 90, 543 (1990)). Anti-sense oligonucleotides are nucleic acid fragments whose base sequence is complementary to an mRNA to be inhibited. This target mRNA can be of cellular, viral or other pathogenic origin. Possible cellular target sequences are, for example, those of receptors, enzymes, immunomodulators, ion channels or oncogenes. The inhibition of virus replication with the aid of anti-sense oligonucleotides was described, for example, for RSV (Rous sarcoma virus), HSV-1 and -2 (herpes simplex virus type I and II), HIV (human immunodeficiency virus) and influenza viruses. In this case, oligonucleotides are employed which are complementary to the viral nucleic acid. Sense oligonucleotides, on the other hand, are designed in their sequence such that they bind ("capture"), for example, nucleic acid-binding proteins or nucleic acid-processing enzymes and thus inhibit their biological activity (Helene, 1990). Viral targets which may be mentioned here are, for example, reverse transcriptase, DNA polymerase and trans-activator proteins. Triplex forming oligonucleotides in general have the DNA as a target and form a triple helical structure after binding to this. While with the aid of the anti-sense oligonucleotides the processing (splicing etc.) of the mRNA or its translation into the protein are in general inhibited, triplex forming oligonucleotides inhibit the transcription or replication of the DNA (Helene et al., 1990, Uhlmann and Peyman, 1990). However, it is also possible to bind single-stranded nucleic acids in a first hybridization with an anti-sense oligonucleotide with formation of a double strand, which then in a second hybridization with a triplex forming oligonucleotide forms a triplex structure. The anti-sense and triplex binding regions can in this case be accommodated either in two separate oligonucleotides or else in one oligonucleotide. A further application of synthetic oligonucleotides are the so-called ribozymes, which destroy the target RNA as a result of their ribonuclease activity (J. J. Rossi and N. Sarver, TIBTECH 8, 179 (1990).

For most applications mentioned, oligonucleotides are not very or completely unsuitable in their naturally occurring form. They must be modified chemically such that they fulfil the specific requirements. In order that oligonucleotides can be employed in biological systems, for example for the inhibition of virus replication, they must fulfil the following prerequisites:

1. They must have an adequate high stability under in vivo conditions, i.e. both in the serum and intracellularly.
2. They must be composed such that they can pass through the cell and nucleus membrane.
3. They must bind to their target nucleic acid under physiological conditions in a base-specific manner in order to display the inhibitory effect.

If the internucleotide phosphate radicals are permanently changed, the properties of the oligonucleotides often change drastically. For example, phosphorothioate oligonucleotides often act in a sequence-non-specific manner.

It is therefore a further object of the invention to make available oligonucleotide analogues having specific activity and increased serum stability, which change back again into their natural phosphodiester oligonucleotides in biological systems (serum, organ, cell).

One or more internucleotide phosphate radicals in the oligonucleotides can be modified as a prodrug. It has been found that oligonucleotides having 3' and/or 5'-terminal prodrug modification are more stable even in the serum than the naturally occurring phosphodiester oligonucleotides.

The invention is not restricted to α- and β-D- or L-ribofuranosides, α- and β-D- or L-desoxyribofuranosides and corresponding carbocyclic five-membered ring analogues, but also applies to oligonucleotide analogues which are built up from other sugar units, for example ring-expanded and ring-contracted sugars, acyclic, ring-bridged or suitable sugar derivatives of a different kind. The invention is furthermore not restricted to the derivatives of the phosphate radical shown by way of example in formula I, but also relates to the known dephospho derivatives.

The oligonucleotides can thus be modified from the natural structure in a variety of ways. Such modifications, which are introduced by methods known per se, are, for example:

a) Modifications of the phosphate bridge

The following may be mentioned by way of example: phosphorothioates, phosphorodithioates, methylphosphonates, phosphoramidates, boranophosphates, phosphate methyl esters, phosphate ethyl esters, phenylphosphonates. Preferred modifications of the phosphate bridge are phosphorothioates, phosphorodithioates and methylphosphonates.

b) Replacement of the phosphate bridge

The following may be mentioned by way of example: replacement by formacetal, 3'-thioformacetal, methylhydroxylamine, oxime, methylenedimethylhydrazo, dimethylene sulphone, silyl groups. The one preferred is the replacement by formacetals and 3'-thioformacetals.

c) Modifications of the sugar

The following may be mentioned by way of example: α-anomeric sugars, 2'-O-methylribose, 2'-O-butylribose, 2'-O-allylribose, 2'-fluoro-2'-deoxyribose, 2'-amino-2'-deoxyribose, α-arabinofuranose, carbocyclic sugar analogues. The preferred modification is that by 2'-O-methylribose and 2'-O-n-butylribose.

d) Modifications of the bases which do not change the specificity of the Watson-Crick base pairing The following may be mentioned by way of example: 5-propynyl-2'-deoxyuridine, 5-propynyl-2'-deoxycytidine, 5-hexynyl-2'-deoxyuridine, 5-hexynyl-2'-deoxycytidine, 5-fluoro-2'-deoxycytidine, 5-fluoro-2'-deoxyuridine, 5-hydroxymethyl-2'-deoxyuridine, 5-methyl-2'-deoxycytidine, 5-bromo-2'-deoxycytidine. Preferred modifications are 5-propynyl-2'-deoxyuridine, 5-hexynyl-2'-deoxyuridine, 5-hexynyl-2'-deoxycytidine and 5-propynyl-2'-deoxycytidine.

e) 3'-3'- and 5'-5'-inversions [e.g. M. Koga et al., J. Org. Chem. 56 (1991) 3757]

f) 5'- and 3'-phosphates, and also 5'- and 3'-thiophosphates.

Exemplary groups which favour intracellular absorption are various lipophilic radicals such as —O—$(CH_2)_x$—$CH_3$, in which x is an integer from 6 to 18, —O—$(CH_2)_n$—CH=CH—$(CH_2)_m$—$CH_3$, in which n and m independently of one another are an integer from 6 to 12, —O—$(CH_2CH_2O)_4$—$(CH_2)_9$—$CH_3$, —O—$(CH_2CH_2O)_8$—$(CH_2)_{13}$—$CH_3$ and —O—$(CH_2CH_2O)_7$—$(CH_2)_{15}$—$CH_3$, but also steroid radicals such as cholesteryl or vitamin radicals such as vitamin E, vitamin A or vitamin D and other conjugates which utilize natural carrier systems, such as bile acid, folic acid, 2-(N-alkyl, N-alkoxy) aminoanthraquinone and conjugates of the mannose and peptides of the corresponding receptors which lead to receptor-mediated endocytosis of the oligonucleotides, such as EGF (epidermal growth factor), bradykinin and PDGF (platelet derived growth factor).

The synthesis of the oligonucleotide is carried out according to processes known to the person skilled in the art such as the triester method, the H-phosphonate method or phosphoramidite method, preferably by standard phosphoramidite chemistry according to Caruthers (M. D. Matteucci and M. H. Caruthers, J. Am. Chem. Soc. 103, 3185 (1981)).

It has further been found that compounds of the formula I in which W is formula II and R is formula II', depending on the base sequence of the DNA moiety, inhibit the expression of specific genes, for example of enzymes, receptors or growth factors, in cell culture and in selected examples in animal models.

Very generally, the present invention extends to the use of compounds of the formula I as therapeutically active constituents of a pharmaceutical. Therapeutically active oligonucleotide derivatives are understood as in general meaning anti-sense oligonucleotides, triple helix-forming oligonucleotides, aptamers or ribozymes, in particular anti-sense oligonucleotides.

The pharmaceuticals of the present invention can be used, for example, for the treatment of illnesses which are caused by viruses, for example by HIV, HSV-1, HSV-2, influenza, VSV, hepatitis B or papilloma viruses.

Anti-sense oligonucleotide derivatives according to the invention, which are active against such targets, have, for example, the following base sequence:

a) against HIV, e.g.

5'-A C A C C C A A T T C T G A A A A T G G-3' (SEQ ID NO:1)　　(I)

or

5'-A G G T C C C T G T T C G G G C G C C A-3' (SEQ ID NO:2)　　(II)

or

5'-G T C G A C A C C C A A T T C T G A A A A T G G A T A A-3' (SEQ ID NO:3)　　(III)

or

5'-G C T A T G T C G A C A C C C A A T T C T G A A A-3' (SEQ ID NO:4)　　(IV)

or

5'-T C G T C G C T G T C T C C G C T T C T T C T T C C T G C C A (SEQ ID NO:5)　　(VI)

or b) against HSV-1, e.g.

5'-G C G G G G C T C C A T G G G G G T C G-3' (SEQ ID NO:6)　　(VII)

The pharmaceuticals of the present invention are also suitable, for example, for the treatment of cancer. For example, in this case oligonucleotide sequences can be used which are directed against targets which are responsible for carcinogenesis or cancer growth. Such targets are, for example:

1) nuclear oncoproteins such as c-myc, N-myc, c-myb, c-fos, c-fos/jun, PCNA, p120
2) cytoplasmic/membrane-associated oncoproteins such as EJ-ras c-Ha-ras, N-ras, rrg, bcl-2, cdc-2, c-raf-1, c-mos, c-src, c-abl
3) cellular receptors such as EGF receptor, c-erbA, retinoid receptors, protein kinase regulatory subunits, c-fms
4) cytokines, growth factors, extracellular matrix such as, for example, CSF-1, IL-6, IL-1a, IL-1b, IL-2, IL-4, bFGF, myeloblastin, fibronectin, Anti-sense oligonucleotides of the formula I according to the invention which are active against such targets have, for example, the following base sequence:

a) against c-Ha-ras, e.g.

5'CAGCTGCAACCCAGC-3' (SEQ ID NO:7)　　(VIII)

c) c-myc, e.g.

5'-G G C T G C T G G A G C G G G G C A C A C-3' (SEQ ID NO:8)　　(IX)

5.-A A C G T T G A G G G G C A T-3' (SEQ ID NO:9)　　(X)

d) c-myb, e.g.

5'-G T G C C G G G G T C T T C G G G C-3' (SEQ ID NO:10)　　(XI)

e) c-fos, e.g.

5'-G G A G A A C A T C A T G G T C G A A A G-3' (SEQ ID NO:11)　　(XII)

5'-C C C G A G A A C A T C A T G G T C G A A G-3' (SEQ ID NO:12)　　(XIII)

5'-G G G G A A A G C C C G G C A A G G G G-3' (SEQ ID NO:13)　　(XIV)

f) p120, e.g.

5'-C A C C C G C C T T G G C C T C C C A C-3' (SEQ ID NO:14)　　(XV)

g) EGF receptor, e.g.

5'-G G G A C T C C G G C G C A G C G C-3' (SEQ ID NO:15)　　(XVI)

5'-G G C A A A C T T T C T T T T C C T C C-3' (SEQ ID NO:16)　　(XVII)

h) p53 tumour suppressor, e.g.

5'-G G G A A G G A G G A G G A T G A G G-3' (SEQ ID NO:17)　　(XVIII)

5'-G G C A G T C A T C C A G C T T C G G A G-3' (SEQ ID NO:18)　　(XIX)

The pharmaceuticals of the present invention are further suitable, for example, for the treatment of illnesses which are affected by integrins or cell-cell adhesion receptors, for example by VLA-4, VLA-2, ICAM, VCAM or ELAM.

Anti-sense oligonucleotide derivatives according to the invention which are active against such targets have, for example, the following base sequence:

a) VLA-4, e.g.

5'-G C A G T A A G C A T C C A T A T C-3' (SEQ ID NO:19)　　(XX)

or b) ICAM, e.g.

5'-C C C C C A C C A C T T C C C C T C T C-3' (SEQ ID NO:20) (XXI)

5'-C T C C C C C A C C A C T T C C C C T C-3' (SEQ ID NO:21) (XXII)

5'-G C T G G G A G C C A T A G C G A G G-3' (SEQ ID NO:22) (XXIII)

c) ELAM-1, e.g.

5'-A C T G C T G C C T C T T G T C T C A G G-3' (SEQ ID NO:23) (XXIV)

5'-C A A T C A A T G A C T T C A A G A G T T C-3' (SEQ ID NO:24) (XXV)

The pharmaceuticals of the present invention are also suitable, for example, for the prevention of restenosis. For example, in this case oligonucleotide sequences can be used which are directed against targets which are responsible for proliferation or migration. Such targets are, for example:

1) nuclear transactivator proteins and cyclins such as c-myc, c-myb, c-fos, c-fos/jun, cyclins and cdc2-kinase
2) mitogenic or growth factors such as PDGF, bFGF, EGF, HB-EGF and TGF-$\beta$.
3) Cellular receptors such as bFGF receptor, EGF receptor and PDGF receptor.

Anti-sense oligonucleotides of the formula I according to the invention which are active against such targets have, for example, the following base sequence:

a) c-myb

5'-G T G T C G G G G T C T C C G G G C-3' (SEQ ID NO:25) (XXVI)

b) c-myc

5'-C A C G T T G A G G G G C A T-3' (SEQ ID NO:26) (XXVII)

c) cdc2-kinase

5'-G T C T T C C A T A G T T A C T C A-3' (SEQ ID NO:27) (XXVIII)

d) PCNA (proliferating cell nuclear antigen of rat)

5'-G A T C A G G C G T G C C T C A A A-3' (SEQ ID NO:28) (XXIX)

Suitable administration forms for compounds of the formula I in which W and R, together with the phosphonate radical carrying them, form an oligonucleotide are topical applications, local applications such as with the aid of a catheter or alternatively injections. For injection, the anti-sense oligonucleotide derivatives are formulated in a liquid solution, preferably in a physiologically acceptable buffer, such as Hank's solution or Ringer's solution. The anti-sense oligonucleotides, however, can also be formulated in solid form and dissolved or suspended before use. The doses preferred for systemic administration are about 0.01 mg/kg to about 50 mg/kg of body weight per day.

The pharmaceuticals can also be used, for example, in the form of pharmaceutical preparations which are administered orally, e.g. in the form of tablets, coated tablets, hard or soft gelatin capsules, solutions, emulsions or suspensions. The inclusion of the pharmaceuticals in liposomes which optionally contain further components such as proteins is an administration form which is also suitable. They can also be administered rectally, e.g. in the form of suppositories or parenterally, e.g. in the form of injection solutions. For the production of pharmaceutical preparations, these compounds can be processed in therapeutically inert organic and inorganic excipients. Examples of such excipients for tablets, coated tablets and hard gelatin capsules are lactose, maize starch or derivatives thereof, tallow and stearic acid or salts thereof. Suitable excipients for the preparation of solutions are water, polyols, sucrose, invert sugar and glucose. Suitable excipients for injection solutions are water, alcohols, polyols, glycerol and vegetable oils. Suitable excipients for suppositories are vegetable and hardened oils, waxes, fats and semi-liquid polyols. The pharmaceutical preparations can also contain preservatives, solvents, stabilizing agents, wetting agents, emulsifiers, sweeteners, colourants, flavourings, salts for changing the osmotic pressure, buffers, coating agents, antioxidants, and also, if appropriate, other therapeutic active compounds.

In-vitro anti HIV tests of the dinucleoside $\alpha$-hydroxymethylarylphosphonates 1–3

In-vitro HIV tests were carried out with the dinucleoside $\alpha$-hydroxymethylarylphosphonates 1–3. As a test system human T lymphocytes (CEM/O) were used. The compounds were additionally tested in a thymidine kinase-deficient T-lymphocyte strain (CEM/TK$^-$). The CEM/O cells were infected both with HIV-1 and with HIV-2. Before the tests, it was ensured that the compounds to be tested were free of free nucleoside (max. 0.5% HPLC) . The results of the test assays are listed in Table 1.

As can be seen from Table 1, all compounds exhibit high activity both against HIV-1 and HIV-2 replication. In contrast to the prodrug forms already described in the literature, the compounds of the formula I according to the invention exhibited no cytotoxic action.

TABLE 1

Results of the anti-HIV in vitro test assays of 1–3, 11–13, 4–6 and 28–30 against HIV-1 and HIV-2 in human T lyphocytes (CEM/O and CEM/TK⁻)

Table 1: Synthesized α-hydroxymethylarylphosphonic acid diesters 1–3

Nucleoside analogues

1: Nucleoside = 2',3'-dideoxythymidine (ddT); 2: Nucleoside = 2',3'-dideoxy-2',3'-didehydrothymidine (d4T); 3: Nucleoside = 3'-Deoxy-3'-azodothymidine (AZT)

| 1–3 | X' | Y | Z |
|---|---|---|---|
| a | NMe$_2$ | H | H |
| b | OCH$_3$ | H | H |
| c | CH$_3$ | H | H |
| d | H | H | H |
| e | Cl | H | H |
| f | H | Cl | Cl |
| g | CN | H | H |
| h | NO$_2$ | H | H |
| i | H | NO$_2$ | H |
| j | NO$_2$ | NO$_2$ | H |
| k | H | NO$_2$ | NO$_2$ |

| Compound | Substituent | Antiviral activity EC$_{50}$$^{a)}$ (µg/ml) CEM/O HIV-1 | HIV-2 | CEM/TK⁻ HIB-2 | Toxicity CC$_{50}$$^{b)}$ (µg/ml) |
|---|---|---|---|---|---|
| 1a | NMe$_2$ | 3.25 ± 1.06 | 7.0 ± 4.24 | >100 | >100 |
| 1b | OCH$_3$ | 0.5 ± 0.0 | 0.55 ± 0.07 | >20 | >20 |
| 1c | CH$_3$ | 3.25 ± 1.06 | 10.0 ± 0.0 | >100 | >100 |
| 1d | H | 2.93 ± 1.85 | 13.3 ± 2.9 | >100 | >100 |
| 1e | Cl | 4.0 ± 0.0 | 4.0 ± 0.0 | >100 | >100 |
| 1f | 2,6-di-Cl | 1.4 ± 0.85 | 2.0 ± 0.0 | >20 | >20 |
| 1g | CN | 3.93 ± 3.10 | 7.7 ± 4.6 | >100 | >100 |
| 1h | NO$_2$ | 2.25 ± 0.35 | 3.0 ± 1.41 | >100 | >100 |
| 1j | 2,4-di-NO$_2$ | 2.0 ± 0.0 | 3.50 ± 0.71 | >100 | >100 |
| 2b | OCH$_3$ | 0.10 ± 0.065 | 0.12 ± 0.06 | >100 | >20 |
| 2c | CH$_3$ | 0.12 ± 0.064 | 0.33 ± 0.24 | >100 | >20 |
| 2d | H | 0.16 ± 0.0 | 0.19 ± 0.19 | >100 | >100 |
| 2e | Cl | 0.10 ± 0.05 | 0.12 ± 0.06 | >100 | >100 |
| 2f | 2,6-di-Cl | 0.056 ± 0.034 | 0.12 ± 0.06 | >20 | >100 |
| 2g | CN | 0.091 ± 0.065 | 0.33 ± 0.24 | >100 | >100 |
| 2h | NO$_2$ | 0.066 ± 0.048 | 0.12 ± 0.06 | >100 | >100 |
| 2j | 2,4-di-NO$_2$ | 0.16 ± 0.0 | 0.33 ± 0.24 | >100 | >100 |

The compounds according to the invention have higher partition coefficients in an octanol/water mixture than the nucleoside analogues on which they are based. They are therefore better passively transportable through biomembranes.

The invention is intended to be illustrated in more detail by the following working examples and by the contents of the Patent Claims.

EXAMPLES

1. Preparation of bis(5'-O-2',3'-dideoxythymidine) hydroxy(4-methylphenyl)methylphosphonate:

904 mg (4.0 mmol) of 2',3'-dideoxythymidine were dried in a high vacuum and then dissolved in 60 ml of dry acetonitrile. This solution were treated with 774 mg (6.0 mmol; 1.07 ml) of diisopropylethylamine and cooled to 0° C. in an ice bath. 404 mg (2.0 mol) of diisopropylamine dichlorophosphine were then added in portions in the course of 15 minutes. After addition was complete, the mixture was stirred for 15 minutes while warming to room temperature. At room temperature, 254 mg (4.0 mmol) of tetrazole and 80 ml of water were added. After stirring for 30 minutes, the solvent was condensed out on the high-vacuum unit. The residue was purified on silica gel with the aid of a gradient of ethyl acetate/methanol (0% to 30% methanol) on the Chromatotron. The product was isolated as a colourless solid (797 mg [1.6 mmol]; 80% yield). 797 mg (1.6 mmol) of 2',3'-ddT-H-phosphonate diester were dissolved in 40 ml of dry tetrahydrofuran and treated with 518 mg (4.8 mmol) of 4-methylbenzaldehyde. 20 ml of dry, previously distilled triethylamine was added to this solution with stirring. After 4 hours at room temperature, the starting material had reacted. Final checking was carried out with the aid of reversed-phase HPLC chromatography. The reaction mixture was neutralized by addition of 20 ml of acetic acid and concentrated to dryness on a rotary evaporator. The residue was purified on the Chromatotron with the aid of a gradient of methylene chloride/methanol (0% to 15% methanol). The product was isolated as a colourless solid after lyophilization (921 mg [1.52 mmol]; 95% yield). For the purification of the compound for the in-vitro anti-HIV tests, a semi-preparative HPLC purification was additionally carried out with an isocratic eluent mixture (30% methanol in acetonitrile).

2. Preparation of bis(5'-O-2',3'-dideoxythymidine) hydroxy (4-dimethylaminophenyl)methylphosphonate:

Analogous procedure as in 1. Instead of 4-methylbenzaldehyde 4-dimethylaminobenzaldehyde was employed here. (Yield 90%).

3. Preparation of bis(5'-O-2',3'-dideoxythymidine) hydroxy (4-methoxyphenyl)methylphosphonate:

Analogous procedure as in 1. Instead of 4-methylbenzaldehyde 4-methoxybenzaldehyde was employed here (yield 87%).

4. Preparation of bis(5'-O-2',3'-dideoxythymidine) hydroxy (phenyl)methylphosphonate:

Analogous procedure as in 1. Instead of 4-methylbenzaldehyde benzaldehyde was employed here (yield 93%).

5. Preparation of bis(5'-O-2',3'-dideoxythymidine) hydroxy (4-chlorophenyl)methylphosphonate:

Analogous procedure as in 1. Instead of 4-methylbenzaldehyde 4-chlorobenzaldehyde was employed here (yield 90%).

6. Preparation of bis(5'-O-2',3'-dideoxythymidine) hydroxy (4-cyanophenyl)methylphosphonate:

Analogous procedure as in 1. Instead of 4-methylbenzaldehyde 4-cyanobenzaldehyde was employed here (yield 86%).

7. Preparation of bis(5'-O-2',3'-dideoxythymidine) hydroxy (4-nitrophenyl)methylphosphonate:

Analogous procedure as in 1. Instead of 4-methylbenzaldehyde 4-nitrobenzaldehyde was employed here (yield 85%).

8. Preparation of bis(5'-O-2',3'-dideoxythymidine) hydroxy (2-nitrophenyl)methylphosphonate:

Analogous procedure as in 1. Instead of 4-methylbenzaldehyde 2-nitrobenzaldehyde was employed here (yield 87%).

9. Preparation of bis(5'-O-2',3'-dideoxythymidine) hydroxy (2,4-dinitrophenyl)methylphosphonate:

Analogous procedure as in 1. Instead of 4-methylbenzaldehyde 2,4-dinitroenzaldehyde was employed here (yield 85%).

10. Preparation of bis(5'-O-2',3'-dideoxythymidine) hydroxy (9-fluorenyl)methylphosphonate:

Analogous procedure as in 1. Instead of 4-methylbenzaldehyde 9-fluorenone was employed here (yield 91%).

11. Preparation of bis(5'-O-2',3'-dideoxythymidine) hydroxy (4-pyridyl)methylphosphonate:

Analogous procedure as in 1. Instead of 4-methylbenzaldehyde 4-pyridylaldehyde was employed here (yield 82%).

12. Preparation of bis(5'-O-2',3'-dideoxythymidine) hydroxy (2,6-dichlorophenyl)methylphosphonate:

Analogous procedure as in 1. Instead of 4-methylbenzaldehyde 2,4-dichlorobenzaldehyde was employed here (yield 96%).

13. Preparation of bis(5'-O-2',3'-dideoxy-2',3'-didehydrothymidine)hydroxy(4-methoxyphenyl) methylphosphonate:

Analogous procedure as in 1. Instead of 2',3'-ddT-H-phosphonate diester, d4T-H-phosphonate diester was employed here and instead of 4-methylbenzaldehyde 4-methoxybenzaldehyde was employed (yield 80%).

14. Preparation of bis(5'-O-2',3'-dideoxy-2',3'-didehydrothymidine)hydroxy(4-methylphenyl) methylphosphonate:

Analogous procedure as in 1. Instead of 2',3'-ddT-H-phosphonate diester, d4T-H-phosphonate diester was employed here (yield 83%).

15. Preparation of bis(5'-O-2',3'-dideoxy-2',3'-didehydrothymidine)hydroxy(phenyl)methylphosphonate:

Analogous procedure as in 1. Instead of 2',3'-ddT-H-phosphonate diester, d4T-H-phosphonate diester was employed here and instead of 4-methylbenzaldehyde benzaldehyde was employed (yield 87%).

16. Preparation of bis(5'-O-2',3'-dideoxy-2',3'-didehydrothymidine)hydroxy(4-chlorophenyl) methylphosphonate:

Analogous procedure as in 1. Instead of 2',3'-ddT-H-phosphonate diester, d4T-H-phosphonate diester was employed here and instead of 4-methylbenzaldehyde 4-chlorobenzaldehyde was employed (yield 86%).

17. Preparation of bis(5'-O-2',3'-dideoxy-2',3'-didehydrothymidine)hydroxy(4-cyanophenyl) methylphosphonate:

Analogous procedure as in 1. Instead of 2',3'-ddT-H-phosphonate diester, d4T-H-phosphonate diester was employed here and instead of 4-methylbenzaldehyde 4-cyanobenzaldehyde was employed (yield 86%).

18. Preparation of bis(5'-O-2',3'-dideoxy-2',3'-didehydrothymidine)hydroxy(4-nitrophenyl) methylphosphonate:

Analogous procedure as in 1. Instead of 2',3'-ddT-H-phosphonate diester, d4T-H-phosphonate diester was employed here and instead of 4-methylbenzaldehyde 4-nitrobenzaldehyde was employed (yield 81%).

19. Preparation of bis(5'-O-2',3'-dideoxy-2',3'-didehydrothymidine)hydroxy(2-nitrophenyl) methylphosphonate:

Analogous procedure as in 1. Instead of 2',3'-ddT-H-phosphonate diester, d4T-H-phosphonate diester was employed here and instead of 4-methylbenzaldehyde 2-nitrobenzaldehyde was employed (yield 86%).

20. Preparation of bis(5'-O-2',3'-dideoxy-2',3'-didehydrothymidine)hydroxy(2,4-dinitrophenyl) methylphosphonate:

Analogous procedure as in 1. Instead of 2',3'-ddT-H-phosphonate diester, d4T-H-phosphonate diester was employed here and instead of 4-methylbenzaldehyde 2,4-dinitrobenzaldehyde was employed (yield 80%).

21. Preparation of bis(5'-O-2',3'-dideoxy-2',3'-didehydrothymidine)hydroxy(4-pyridyl) methylphosphonate:

Analogous procedure as in 1. Instead of 2',3'-ddT-H-phosphonate diester, d4T-H-phosphonate diester was employed here and instead of 4-methylbenzaldehyde 4-pyridylaldehyde was employed (yield 80%).

22. Preparation of bis(5'-O-2',3'-dideoxy-2',3'-didehydrothymidine)hydroxy(2,6-dichlorophenyl) methylphosphonate:

Analogous procedure as in 1. Instead of 2',3'-ddT-H-phosphonate diester, d4T-H-phosphonate diester was employed here and instead of 4-methylbenzaldehyde 2,6-dichlorobenzaldehyde was employed (yield 87%).

23. Preparation of bis(5'-O-2',3'-dideoxy-2',3'-didehydrothymidine)hydroxyheptylmethylphosphonate:

Analogous procedure as in 1. Instead of 2',3'-ddT-H-phosphonate diester, d4T-H-phosphonate diester was employed here and instead of 4-methylbenzaldehyde octanal was employed (yield 75%).

24. Preparation of bis(5'-O-2',3'-dideoxy-3'-azidothymidine) hydroxy(4-nitrophenyl)methylphosphonate:

Analogous procedure as in 1. Instead of 2',3'-ddT-H-phosphonate diester, AZT-H-phosphonate diester was employed here and instead of 4-methylbenzaldehyde 4-nitrobenzaldehyde was employed (yield 96%).

25. Preparation of bis(5'-O-2',3'-dideoxy-3'-azidothymidine) hydroxy(2-nitrophenyl)methylphosphonate:

Analogous procedure as in 1. Instead of 2',3'-ddT-H-phosphonate diester, AZT-H-phosphonate diester was employed here and instead of 4-methylbenzaldehyde 2-nitrobenzaldehyde was employed (yield 92%).

26. Preparation of bis(5'-O-2',3'-dideoxy-3'-azidothymidine) hydroxy(2,6-dinitrophenyl)methylphosphonate:

Analogous procedure as in 1. Instead of 2',3'-ddT-H-phosphonate diester, AZT-H-phosphonate diester was employed here and instead of 4-methylbenzaldehyde 2,6-dinitrobenzaldehyde was employed (yield 88%).

27. Preparation of bis(5'-O-2',3'-dideoxy-3'-azidothymidine) hydroxy(2,4-dinitrophenyl)methylphosphonate:

Analogous procedure as in 1. Instead of 2',3'-ddT-H-phosphonate diester, AZT-H-phosphonate diester was employed here and instead of 4-methylbenzaldehyde 2,4-dinitrobenzaldehyde was employed (yield 90%).

28. Preparation of bis(5'-O-2',3'-dideoxy-3'-azidothymidine) hydroxy(4-pyridyl)methylphosphonate:

Analogous procedure as in 1. Instead of 2',3'-ddT-H-phosphonate diester, AZT-H-phosphonate diester was employed here and instead of 4-methylbenzaldehyde 4-pyridylaldehyde was employed (yield 96%).

29. Preparation of bis(5'-O-2',3'-dideoxy-3'-azidothymidine) hydroxyheptylmethylphosphonate:

Analogous procedure as in 1. Instead of 2',3'-ddT-H-phosphonate diester, AZT-H-phosphonate diester was employed here and instead of 4-methylbenzaldehyde octanal was employed (yield 96%).

30. Preparation of (5'-O-2',3'-dideoxy-3'-azidothymidine)-(5'-O-2',3'-dideoxythymidine)hydroxy(2,6-dinitrophenyl) methylphosphonate:

Analogous procedure as in 1. Instead of 2',3'-ddT-H-phosphonate diester, ddT/AZT-H-phosphonate diester was employed here and instead of 4-methylbenzaldehyde 2,6-nitrobenzaldehyde was employed (yield 88%).

31. Preparation of(5'-O-2',3'-dideoxy-3'-azidothymidine)-(5'-O-2',3'-dideoxy-2,3-didehydrothymidine)hydroxy(4-nitrophenyl)methylphosphonate:

Analogous procedure as in 1. Instead of 2',3'-ddT-H-phosphonate diester, d4T/AZT-H-phosphonate diester was employed here and instead of 4-methylbenzaldehyde 4-nitrobenzaldehyde was employed (yield 96%).

32. Preparation of(5'-O-2',3'-dideoxy-3'-azidothymidine)-(5'-O-2',3'-dideoxy-2,3-didehydrothymidine)hydroxy(2,6-dinitrophenyl)methylphosphonate:

Analogous procedure as in 1. Instead of 2',3'-ddT-H-phosphonate diester, d4T/AZT-H-phosphonate diester was employed here and instead of 4-methylbenzaldehyde 2,6-dinitrobenzaldehyde was employed (yield 87%).

40. Preparation of(5$^1$-O-2',3'-dideoxythymidine)-(5'-O-2',3'-dideoxy-2,3-didehydrothymidine)hydroxy(2-nitrophenyl) methylphosphonate:

Analogous procedure as in 1. Instead of 2',3'-ddT-H-phosphonate diester, d4T/ddT-H-phosphonate diester was employed here and instead of 4-methylbenzaldehyde 2-nitrobenzaldehyde was employed (yield 91%).

41. Preparation of (5'-O-thymidine)-(5'-O-2',3'-dideoxy-2',3'-didehydrothymidine)hydroxy(2-nitrophenyl) methylphosphonate:

Analogous procedure as in 1. Instead of 2',3'-ddT-H-phosphonate diester, d4T/T-H-phosphonate diester was employed here and instead of 4-methylbenzaldehyde 2-nitrobenzaldehyde was employed (yield 85%).

42. Preparation of bis(5'-O-3'-O)-levulinylthymidine hydroxy(4-chlorophenyl)methylphosphonate:

Analogous procedure as in 1. Instead of 2',3'-ddT-H-phosphonate diester, 3'-levulinylthymidine-H-phosphonate diester was employed here and instead of 4-methylbenzaldehyde 4-chlorobenzaldehyde was employed (yield 93%).

43. Preparation of bis(5'-O-3'-O-t-butyldimethylsilylthymidine)hydroxy(4-chlorophenyl) methylphosphonate:

Analogous procedure as in 1. Instead of 2',3'-ddT-H-phosphonate diester, 3'-levulinylthymidine-H-phosphonate diester was employed here and instead of 4-methylbenzaldehyde 4-chlorobenzaldehyde was employed (yield 85%).

44. Preparation of bis(5'-O-3'-O-acetylthymidine)hydroxy-(4-chlorophenyl)methylphosphonate:

Analogous procedure as in 1. Instead of 2',3'-ddT-H-phosphonate diester, 3'-acetylthymidine-H-phosphonate diester was employed here and instead of 4-methylbenzaldehyde 4-chlorobenzaldehyde was employed (yield 75%).

45. Preparation of bis (5'-O-3'-O-acetylthymidine)hydroxy-(4-methoxyphenyl)methylphosphonate:

Analogous procedure as in 1. Instead of 2',3'-ddT-H-phosphonate diester, 3'-acetylthymidine-H-phosphonate diester was employed here and instead of 4-methylbenzaldehyde 4-methoxybenzaldehyde was employed (yield 70%).

46. Preparation of bis(5'-O-thymidine) hydroxy(4-chlorophenyl)methylphosphonate:

Preparation was carried out from the 3'-O-levulinyl-protected derivative described in 5a) according to standard conditions with the aid of 5 equivalents of hydrazine hydrate in pyridine/acetic acid 4:1 in the course of 15 minutes at room temperature.

47. Preparation of di(5'-O-2',3'-dideoxy-2',3'-didehydrothymidine)phosphite:

Analogous procedure as in 1. Instead of 2',3'-dideoxythymidine 2',3'-dideoxy-2',3'-didehydrothymidine was employed (yield 75%).

48. Preparation of di(5'-O-2',3'-dideoxy-3'-azidothymidine) phosphite:

Analogous procedure as in 1. Instead of 2',3'-dideoxythymidine, 2',3'-dideoxy-3'-azidothymidine was employed (yield 85%).

49. Preparation of di(5'-O-3'-levulinylthymidine)phosphite:

Analogous procedure as in 1. Instead of 2',3'-dideoxythymidine, 3'-levulinylthymidine was employed (yield 65%).

50. Preparation of di(5'-O-3'-t-butyldimethylsilylthymidine) phosphite:

Analogous procedure as in 1. Instead of 2',3'-dideoxythymidine, 3'-t-butyldimethylsilylthymidine was employed (yield 65%).

51. Preparation of di (5'-O-3'-acetylthymidine) phosphite:

Analogous procedure as in 1. Instead of 2',3'-dideoxythymidine, 3'-acetylthymidine was employed (yield 86%).

The reactions with the strongly acceptor-substituted benzaldehydes (4-nitro-, 2-nitro-, and 2,4-dinitrobenzaldehyde) could also be carried out using the chiral quinine as a base. The reactions with the donor-substituted benzaldehydes (4-dimethylamino-, 4-methoxy-, 4-methyl- and benzaldehyde) were also carried out in pure triethylamine with heating alternatively to the experiments described above.

52. Preparation of 5'-O-(4,4'-dimethoxytrityl)thymidylyl (3'5')-thymidine-3'-((O-triethylsiloxy)-2-nitrobenzyl) phosphonate (TES-protected hydroxy-3'-OH phosphonate dimer D):

a) Preparation of 5'-O-(4,4'-dimethoxytrityl)thymidylyl-(3'5')-3'-O-levulinylthymidine-3'-H-phosphonate:

(H-phosphonate dimer A)

1.9 g (2.7 mmol; 1.1 eq.) of 5'-O-(4,4¹-dimethoxytrityl) thymidylyl-3'-H-phosphonate were dried in a high vacuum and dissolved in 30 ml of dry pyridine. 828 mg (2.4 mmol; 1.0 eq.) of predried 3'-O-levuinylthymidine were added to this solution. 899 ml of freshly distilled pivaloyl chloride were then added dropwise and stirring was continued at room temperature. After 8 min, the mixture was diluted with 150 ml of methylene chloride and extracted in a separating funnel using 150 ml of 5% strength sodium hydrogen carbonate solution. After extraction a further two times using 150 ml of methylene chloride each time, the extract was dried over sodium sulphate, filtered off from the drying agent and concentrated to dryness on a rotary evaporator. The crude product was purified by means of flash chromatography. The gradient of the eluent ethyl acetate/methanol (+addition of 0.1% acetic acid) was increased from 0% to 5% methanol.

The product was isolated as a yellow solid (1.972 g; 2.12 mmol; 78%).

b) Preparation of 5'-O-(4,4'-dimethoxytrityl)thymidylyl-(3'5')-3'-O-levulinylthymidine-3'-((-hydroxy)-2-nitrobenzyl)phosphonate:

(α-hydroxyphosphonate dimer B)

1.5 g (1.6 mmol; 1 eq.) of the H-phosphonate dimer A were dissolved in predried form in 20 ml of dry methylene chloride. This solution was treated with 725 mg (4.8 mmol; 3 eq.) of predried 2-nitrobenzaldehyde and then with 40 ml of triethylamine. After stirring at room temperature for 8 hours, it was neutralized with acetic acid and the solution was purified directly by means of flash chromatography. The gradient of the eluent methylene chloride/methanol (+addition of 0.1% acetic acid) was increased from 0% to 5% methanol.

The product is a colourless solid (1.374 g; 1.27 mmol; 79%).

c) Preparation of 5'-O-(4,4'-dimethoxytrityl)thymidylyl-(3'5')-3'-O-levulinylthymidine-3'-((-O-triethylsiloxy)-2-nitrobenzyl)phosphonate:

(TES-protected hydroxyphosphonate dimer C)

1.1 g (1.01 mmol; 1 eq.) of -hydroxyphosphonate dimer B were dissolved in predried form in 20 ml of dry pyridine. 914 mg (6.07 mmol; 1.02 ml; 6 eq.) of triethylsilyl chloride were added dropwise to this solution and it was stirred at room temperature. After stirring for seven hours, it was concentrated to dryness on a rotary evaporator.

The crude product was purified by means of flash chromatography. The gradient of the eluent ethyl acetate/methanol was increased from 0% to 4% methanol. The product is a pale yellow solid (1.13 g; 0.95 mmol; 93%).

d) Preparation of 5'-O-(4,4'-dimethoxytrityl)thymidylyl-(3'5')-thymidine-3'-((-O-triethylsiloxy)-2-nitrobenzyl) phosphonate (D):

1.1 g (0.92 mmol) of TES-protected hydroxyphosphonate dimer C were dissolved in 10 ml of pyridine and treated with 10 ml of a solution of 3 ml of hydrazine hydrate (24% in water), 6.92 ml of pyridine and 4.61 ml of acetic acid. After stirring at room temperature for three minutes, the solution was cooled to 0° C. and diluted with 100 ml of water and 100 ml of ethyl acetate. After separating the phases in a separating funnel, the organic phase was washed once with 25 ml of a 5% strength sodium hydrogen carbonate solution and then dried over sodium sulphate. After separating off the drying agent, it was concentrated to dryness on a rotary evaporator. The crude product was purified by means of flash chromatography. The gradient of the eluent methylene chloride/methanol was increased from 0% to 7% methanol.

The product was isolated as a pale yellow solid (858 mg; 0.78 mmol; 85%).

53. Preparation of 5'-O-(4,4'-dimethoxytrityl)thymidylyl-(3'5')thymidine-3'-O-(β-cyanoethyldiisopropylaminophosphoramidite)-((O-triethylsiloxy)-2-nitrobenzyl)phosphonate (TES-protected hydroxy-3'-phosphoramiditephosphonate dimer E)

230 mg (0.21 mmol; 1 eq.) of TES-protected hydroxy-3'-OH phosphonate dimer D were dissolved in predried form in 15 ml of dry methylene chloride, treated with stirring with 177 ml (1.05 mmol; 135 mg; 5 eq) of diisopropylethylamine and then with 70 ml (0.31 mmol; 74.2 mg; 1.5 eq) of β-cyanoethyldiisopropylchlorophosphine. The mixture was stirred at room temperature for 5 hours, 20 ml of ethyl acetate was added and it was concentrated to dryness on a rotary evaporator. It was then extracted twice with 20 ml of 2% strength sodium hydrogen carbonate solution each time followed by saturated sodium chloride solution. The organic phase was dried over sodium sulphate. After filtration, the residue was concentrated to dryness on a rotary evaporator.

The crude product was purified by means of flash chromatography. As an eluent, methylene chloride/acetonitrile 1:1 (+addition of 1% triethylamine) was used. The product is a pale yellow solid (123 mg; 0.095 mmol; 45%).

54. Preparation of 5'-O-(4,4'-dimethoxytrityl)thymidylyl-(3'→5')thymidine-3'-O-succinyl((-O-triethylsiloxy)-2-nitrobenzyl)phosphonate (TES-protected hydroxy-3'-succinylphosphonate dimer F)

200 mg (0.18 mmol; 1.4 eq) of TES-protected hydroxy-3'-OH-phosphonate dimer D were dissolved in predried form in 2 ml of dry pyridine. 24.4 mg (0.2 mmol) of 4-dimethylaminopyridine and 20.0 mg (0.2 mmol) of succinic anhydride were then added successively and the mixture was allowed to react at room temperature for 4 hours with stirring. 45 ml of water were added and, after stirring for 10 minutes, the mixture was concentrated to dryness on a rotary evaporator. The residue was taken up in 15 ml of methylene chloride and extracted once with 8 ml of cold 10% strength citric acid and twice with 8 ml of cold water each time. The organic phase was then dried over sodium sulphate. After filtration, it was concentrated to dryness on a rotary evaporator. The crude product was taken up in 3 ml of methylene chloride and added dropwise to 25 ml of ice-cold n-hexane. The product was deposited as a colourless precipitate. To complete the precipitation, the mother liquor was stored at −20° C. for a few hours, then the solid was filtered off and dried. The product is a colourless solid (167 mg; 0.14 mmol; 78%).

55. Preparation of 5'-O-(4,4'-dimethoxytrityl)thymidylyl-(3'→5')thymidine-3'-O-succinyl-CPG((α-O-triethylsiloxy)-2-nitrobenzyl)phosphonate (CPG-bound TES-protected hydroxy-3'-succinylphosphonate dimer G)

50 mg (0.042 mmol; 1.5 eq.) of TES-protected hydroxy-3'-succinylphosphonate dimer F were dissolved in 1.5 ml of dry dimethylformamide in a Pierce flask and treated with 13.41 mg (0.042 nmol; 1.5 eq.) of O-benzotriazol-1-yl-N,N,N',N',-tetramethyluronium tetrafluoroborate (TBTU) and 4.2 ml (0.033 mmol; 3.84 mg; 1.2 eq.) of N-ethylmorpholine. 370 mg of CPG support were then added and the mixture was shaken at room temperature for a further 4 hours. It was transferred to a frit, washed with methanol and methylene chloride, transferred to the Pierce flask again and treated with 1.5 ml of capping reagent. It was shaken for a further hour, again transferred to a frit, filtered off, washed with methanol, methylene chloride, tetrahydrofuran and diethyl ether and dried at 40° C. in an oil pump vacuum.

Loading of the support: 47.12 mmol/g

56. Preparation of an oligonucleotide of the formula

TTTTTTTTT(pp)T (SEQ ID NO:29)

(pp is an α-hydroxy(o-nitrophenyl)methylphosphonate bridge)

The CPG support from Example 55, which contains 1 μmol of the dinucleotide bonded via the 3'-end, is successively treated with the following reagents:

1. Acetonitrile abs.
2. 2% dichloroacetic acid in dichloromethane
3. Acetonitrile abs.
4. 10 μmol of β-cyanoethyl 5'-O-dimethoxytritylthymidine-3'-phosphatediisopropylamidite and 40 μmol of tetrazole in acetonitrile abs.
5. Acetonitrile
6. 20% acetic anhydride in THF containing 40% lutidine and 10% dimethylaminopyridine
7. Acetonitrile
8. Iodine (1.3 gr in THF/water/pyridine; 70:20:5=v:v:v)

Steps 1 to 8, subsequently called a reaction cycle, are repeated 7 times to synthesize the decathymidylate derivative. After synthesis has been concluded, the dimethoxytrityl group is removed as described in steps 1 to 3. By treatment with ammonia, the oligonucleotide is cleaved from the support and at the same time the β-cyanoethyl groups are eliminated. The silyl protective group is removed by treatment with 80% strength acetic acid. The decathymidylate derivative crude product obtained, which at the 3'-end contains a (-hydroxy-o-nitrophenylmethylphosphonate) internucleotide bond, is purified by polyacrylamide gel electrophoresis or HPLC.

57. Preparation of an oligonucleotide of the formula

T(pp)TTTTTTTT (SEQ ID NO:30)

Commercially obtainable CPG support, which contains 1 μmol of the 5'-O-dimethoxytritylthymidine bonded via the 3'-end, is treated successively with the following reagents:

1. Acetonitrile abs.
2. 2% dichloroacetic acid in dichloromethane
3. Acetonitrile abs.
4. 10 μmol of β-cyanoethyl 5'-O-dimethoxytritylthymidine-3'-phosphite diisopropylamidite and 40 μmol of tetrazole in acetonitrile abs.
5. Acetonitrile
6. 20% acetic anhydride in THF containing 40% lutidine and 10% dimethylaminopyridine
7. Acetonitrile
8. Iodine (1.3 gr in THF/water/pyridine; 70:20:5=v:v:v)

Steps 1 to 8, subsequently called a reaction cycle, are repeated 7 times to synthesize the decathymidylate derivative. In the last cycle, instead of the monomer in step 4 the corresponding dinucleotide, which was prepared as in Example 53, is employed. After synthesis has been concluded, the dimethoxytrityl group is removed as described in steps 1 to 3. By treatment with ammonia, the oligonucleotide is cleaved from the support and at the same time the β-cyanoethyl groups are eliminated. The silyl protective group is removed by treatment with 80% strength acetic acid. The decathymidylate derivative crude product obtained, which at the 5'-end contains a (-hydroxy-o-nitrophenylmethylphosphonate)internucleotide bond, is purified by polyacrylamide gel electrophoresis or HPLC.

58. Preparation of an oligonucleotide of the formula:

T(pp)TTTTTTT(pp)T (SEQ ID NO:31)

(pp is in each case an α-hydroxy(o-nitrophenyl) methylphosphonate bridge)

Synthesis is carried out in an analogous manner to that described in Example 56 starting from T(pp)T-CPG support from Example 55, which contains 1 μmol of the dinucleotide bonded via the 3'-end. In the last cycle, instead of the monomer in step 4, the corresponding dinucleotide which was prepared as in Example 53, is employed. After synthesis has been concluded, the dimethoxytrityl group is removed as described in steps 1 to 3. By treatment with ammonia, the oligonucleotide is cleaved from the support and at the same time the β-cyanoethyl groups are eliminated. The silyl protective group is removed by treatment with 80% strength acetic acid. The decathymidylate derivative crude product obtained, which at the 3'-end and at the 5'-end in each case contains a (-hydroxy-o-nitrophenylmethylphosphonate) internucleotide bond, is purified by polyacrylamide gel electrophoresis or HPLC.

59. Preparation of GCAGGAGGATGCTGAGGAGG(pp)C (SEQ ID NO:32) (HSV target)

Preparation is carried out analogously to that described in Example 56, starting from corresponding G(pp)C-CPG support instead of T(pp)T-CPG. In the condensation reactions, in step 4 in each case the monomer building block of deoxyadenosine, deoxyguanosine or deoxycytidine corresponding to the sequence are employed. Those commercially obtainable building blocks which have rapidly removable protective groups (^R Expedite Fast Deprotecting Amidites; Millipore, Eschborn) are preferred.

60. Preparation of G(pp)CAGGAGGATGCTGAGGAGG(pp)C (SEQ ID NO:33)

Preparation is carried out in an analogous manner to that described in Example 5, the corresponding G(pp)C phosphoramidite being employed in the last condensation step instead of the T(p)T phosphoramidite.

61. Preparation of G(pp)CAGGAGGATG(pp)CTGAGGAGG(pp)C (SEQ ID NO:34)

Preparation is carried out in an analogous manner to that described in Example 5, the corresponding G(pp)C phosphoramidite being employed in each case in the eighth and in the last condensation step.

62. Preparation of G(pp)CGGGGCTCCATGGGGGTC(pp)G (SEQ ID NO:35)

Preparation is carried out in an analogous manner to that described in Example 60, starting from corresponding C(pp)G-CPG support instead of G(pp)C-CPG.

63. Preparation of C(pp)GAGAACATCATGGTC(pp)G (SEQ ID NO:36) (c-fos Target)

Preparation is carried out in an analogous manner to that described in Example 62, the corresponding C(pp)G phosphoramidite being employed in the last cycle.

64. Characterization of the oligonucleotides

Characterization is carried out with the aid of HPLC, polyacrylamide gel electrophoresis (PAGE) and negative ion electrospray mass spectrometry (ES-MS⁻). The products are purified as described above and afterwards exhibit a homogeneous band in the PAGE (20% acrylamide, 2% bisacrylamide and 7M urea). HPLC is carried out on reversed phase columns RP-18 from Merck or on a PA-100 column from Dionex.

For the ES-MS⁻, the oligonucleotides are converted into the ammonium salts by ammonium acetate precipitation or other salt exchange. The sample application is carried out from a solution in acetonitrile/water (1:1) containing 5 $OD_{260}$/ml of oligomer. The accuracy of the method is about ±1.5 Daltons.

65. Procedure for Determination of the stability and cell absorption after radioactive labelling Radioactive labelling:

A generally applicable procedure for labelling with $^{35}S$ consists in carrying out at least one oxidation in the DNA synthesis cycle (step 20 in Example 11) using elemental $^{35}$sulphur in the synthesis of the oligonucleotide. Oligonucleotides which have a free 5'-hydroxy group can be labelled with $^{32}P$ or $^{35}S$ by methods which are known per se with the aid of the polynucleotide kinase. Oligonucleotides which carry a free 3'-hydroxy group can be labelled in a known manner with 3'-terminal transferase. As an example, the 5'-labelling of the DNA moiety is presented here: the oligonucleotide having a free 5'-hydroxy group (500 pmol) is dissolved in 420 µl of water, and this solution is heated to 90° C. and chilled. 50 µl of 10× kinase buffer and 50 µl of $^{32}P$ gamma-ATP (6000 Ci/mmol) or $^{35S}$-gamma-ATP are then added and the mixture is incubated at 37° C. for 1 hour. The reaction is stopped by addition of 0.5M EDTA solution. Desalting is carried out with the aid of an NAPR column from Pharmacia.

Investigation of the stability of the oligomer in the medium containing cells:

The supernatant 1 (10 µl) can be mixed with 5 µl of 80% formamide (with XC and BB), heated at 95° C. (5 minutes) and loaded onto a polyacrylamide gel (20% acrylamide, 7M urea). After the development of the gel in an electrical field, the bands on the gel can be allocated by means of autoradiography to the "stable oligomer" or the missing bands to the "degraded oligomer". Result after an incubation time of 24 hours: in comparison with the unmodified oligonucleotides, the compounds of the formula I (W equals formula II, R equals formula II') should all have a greatly increased lifetime.

Procedure for determination of the cell uptake:

Vero cells can be incubated in 96-well microtitre plates in DMEM, 5% FCS for 24 hours at 37° C. After the medium has been removed, the cells can be washed a further two times with serum-free DMEM. The radiolabelled oligomer ($10^6$ cpm) is diluted to a concentration of 10 µm in serum using unlabelled oligomer and the cells are incubated with it at 37° C. After 1, 7 and 24 hours, 150 µl in each case are removed (designation: "supernatant 1"). The cells in the wells of the microtitre plates are washed 7 times with 300 µl of fresh medium and the combined wash media (designation: "supernatant 2") measured in a scintillation counter. 100 µl of trypsin solution are then added, 30 seconds are waited and the supernatant is stripped off. To detach the cells from the plate, it is incubated at 37° C. for 3 min. The detached cells are transferred to 1.5 ml Eppendorf vessels and centrifuged at 2000 rpm for 6 minutes ("supernatant 3"). The supernatants 1 (5 µl), 2 and 3 (0.5 ml) are in each case measured separately in the scintillation counter. From this is calculated the uptake of the oligomer in pmol per 100,000 cells, supernatant 3 being the cell-bound oligomer fraction and the sum of supernatants 1 and 2 the non-cell-bound oligomer fraction.

66. Procedure for determination of the cell uptake after fluorescence labelling:

The COS cells can be allowed to grow to confluence in Dulbecco's MEM, which is supplemented with 10% FCS, in 5 cm Petri dishes. The cells are washed twice with serum-free DMEM. With the aid of a sterile needle, an area of about 1 cm² in the centre of the Petri dish is scraped. The DNA oligomer solution (0.1 mM) to be investigated is applied to this area. It is incubated at 37° C. under a $CO_2$ atmosphere. After 2, 4 and 16 hours, the cells are investigated by fluorescence microscopy. For this purpose, the cells are washed four times with serum-free DMEM, covered with a glass support and assessed under the fluorescence microscope or by phase contrast.

67. Determination of the melting temperatures:

The melting temperatures are determined with the aid of an HP 8452A diode array spectrophotometer, an HP 89090A Peltier element and the HP temperature control software Rev. B5.1 (Hewlett Packard). It is measured in 0.5° C./min steps in 10 mM HEPES and 140 mM NaCl (pH 6.5) as buffer. The oligomer concentration is 0.5 to 1.5 $OD_{260}$ per ml.

68. Testing for antiviral activity in cell culture:

The antiviral activity of the test substances against various human pathogenic herpes viruses is investigated in a cell culture test system. For the test, monkey kidney cells (Vero, $2\times10^5$/ml) are seeded in serum-containing Dulbecco's MEM (5% foetal calf serum FCS) in 96-well microtitre plates and incubated for 24 h at 37° C. and 5% $CO_2$. The serum-containing medium is then aspirated and the cells are washed twice with serum-free Dulbecco's MEM (-FCS). The test substances are prediluted to a concentration of 600 µM in $H_2O$ and stored at −18° C. For the test, further dilution steps in Dulbecco's minimal essential medium (MEM) are carried out. 100 µl each of the individual test substance dilutions are added to the washed cells together with 100 µl of serum-free Dulbecco's MEM (-FCS). After incubation at 37° C. and 5% $CO_2$ for 3 h, the cells are infected with herpes simplex virus type 1 (ATCC VR733, HSV-1 F-strain) or with herpes simplex virus type 2 (ATCC VR734, HSV-2 G-strain) in concentrations at which the cell lawn should be completely destroyed within 3 days. In the case of HSV-1, the infection potency is 500 plaque-forming units (PFU) per well, in the case of HSV-2 350 PFU/well. The experimental batches then should contain test substance in concentrations of 80 µM to 0.04 µM in MEM, supplemented by 100 U/ml of penicillin G and 100 mg/l of streptomycin. All experiments should be carried out as a double determination with the exception of the controls, which are carried out eight times per plate. The experimental batches are incubated for 17 h at 37° C. and 5% $CO_2$. The cytotoxicity of the test substances is determined after a total incubation time of 20 h by microscopic assessment of the cell cultures. The maximum tolerated dose (MTD) is designated as the highest preparation concentration which under the said experimental conditions still does not produce any microscopically detectable cell damage. After this, FCS is added to a final concentration of 4% with further incubation for 55 h at 37° C. and 5% $CO_2$. The untreated infection controls then exhibit a complete cytopathic effect (CPE). After microscopic assessment of the cell cultures, these are then stained with Neutral Red according to the vital staining method of Finter (1966). The antiviral activity of a test substance is defined as the minimum inhibitory concentration (MIC) which is needed in order to protect 30–60% of the cells from the virus-related cytopathogenic effect. The MIC values of various oligonucleotides are in the range from 0.1 to 80 µmol/l.

69. Procedure for determination of the in vivo activity against viruses

For the testing of the compounds in vivo, 5 week-old NMRI mice having a weight of approximately 16 to 18 grams can be employed. The mice are kept under conventional conditions in groups of up to five animals and with food and water ad libitum. The mice can be infected intraperitoneally with about 10 to 50 LD50 units of an HSV strain (HSV "corneae"). The compound would be administered twice daily i.p. at 1, 10 or 50 mg/kg. The control animals receive a 1% strength sodium chloride solution. The survival rate of the animals is monitored over a period of 2 weeks. When the anti-sense oligonucleotides are administered there are expected to be 1 to 5 survivors, while after placebo administration all animals are expected to die.

70. Procedure for determination of the in vivo activity: Inhibition of c-Fos protein expression in the rat:

Determination can be carried out as described (Sandkühler et al. (1991) in: Proceedings of the VIth World Congress on Pain, Charlton and Woolf, Editors; Elsevier, Amsterdam; page 313–318) by superfusion of the spinal cord. After laminectomy of a barbiturate anaesthetized Sprague-Dawley rat, a two-chamber container made of silicone is fashioned for containing the anti-sense oligomer. One chamber is filled with the anti-sense oligonucleotide derivative, while the other chamber is filled with the control oligomer (concentration 75 μm each). In each case, the superfusate is exchanged after one hour. After superfusion for 6 hours, c-fos expression is stimulated by heat treatment (52° C.) of the hind legs. The inhibition of c-fos expression can be detected immunohistochemically on appropriate tissue section samples.

71. Preparation of 5'-O-(4,4'-dimethoxytriphenylmethyl)2'-deoxythymidylyl-(3'→5')-3'-O-levulinyl-2'-deoxythymidine 3'-((α-O-tributylsiloxy)-2-nitrobenzyl)phosphonate:

TBS(tributylsiloxy)-protected hydroxyphosphonate dimer H)

1.77 g (1.636 mmol; 1 eq.) of α-hydroxyphosphonate dimer B were dissolved in predried form in 30 ml of dry pyridine. 2.62 ml (9.816 mmol; 2.306 g; 6 eq.) of chlorotributylsilane were added dropwise to this solution. After stirring at room temperature for 8 hours, the reaction was terminated by addition of methanol and the mixture was concentrated to dryness on a rotary evaporator.

The crude product was purified by means of flash chromatography. The gradient of the eluent ethyl acetate/methanol was increased from 0% to 2% methanol. The product is a pale yellow solid (1.78 g; 1.39 mmol; 85%).

72. Preparation of 5'-O-(4,4'-dimethoxytriphenylmethyl)-2'-deoxythymidylyl-(3'→5')-2'-deoxythymidine 3'-((α-O-tributylsiloxy)-2-nitrobenzyl)phosphonate:

(TBS-protected hydroxy-3'-OH-phosphonate dimer I)

1.2 g (0.94 mmol) of TBS-protected hydroxyphosphonate dimer H were dissolved in 10 ml of pyridine and treated with 10 ml of a solution of 3 ml of hydrazine hydrate (24% in water), 6.92 ml of pyridine and 4.61 ml of acetic acid. After stirring at room temperature for 3 minutes, the solution was cooled to 0° C. and diluted with 100 ml of water and 100 ml of ethyl acetate. After separating the phases in a separating funnel, the organic phase was washed once with 25 ml of a 5% strength sodium hydrogen carbonate solution and then dried over sodium sulphate. The drying agent was filtered off and the filtrate was concentrated to dryness on a rotary evaporator.

The crude product was purified by means of flash chromatography. The gradient of the eluent methylene chloride/methanol was increased from 0% to 5% methanol. The product was isolated as a pale yellow solid (910 mg; 0.77 mmol; 82%).

73. Preparation of 5'-O-(4,4'-dimethoxytriphenylmethyl)-2'-deoxythymidylyl-(3'→5')-2'-deoxythymidine 3'-O-succinyl-((α-O-tributylsiloxy)-2-nitrobenzyl)phosphonate (TBS-protected hydroxy-3'-succinylphosphonate dimer J)

120 mg (0.10 mmol; 1 eq) of TBS-protected hydroxy-3'-OH-phosphonate dimer I were dissolved in predried form in 1 ml of dry pyridine. 14.8 mg (0.12 mmol; 1.2 eq.) of 4-dimethylaminopyridine and 12.1 mg (0.12 mmol; 1.2 eq.) of succinic anhydride were then added successively and the mixture was stirred at room temperature for 4 hours. 40 ml of water were added and, after stirring for 10 minutes, the mixture was concentrated to dryness on a rotary evaporator. The residue was taken up in 10 ml of methylene chloride and extracted once with 5 ml of cold 10% strength citric acid and twice with 5 ml of cold water each time. The organic phase was then dried over sodium sulphate. After filtration, the filtrate was concentrated to dryness on a rotary evaporator.

The crude product was taken up in 3 ml of methylene chloride and added dropwise to 25 ml of ice-cold n-hexane. The product was deposited as a colourless precipitate. To complete the precipitation, the mother liquor was stored at −20° C. for a few hours, then the solid was filtered off and dried. The product is a colourless solid (115 mg; 0.09 mmol; 90%).

74. Preparation of 5'-O-(4,4'-dimethoxytriphenylmethyl)-2'-deoxythymidylyl-(3'→5')-2'-deoxythymidine 3'-O-succinyl-CPG((α-O-tributylsiloxy)-2-nitrobenzyl)phosphonate:

(CPG-bound TBS-protected hydroxy-3'-succinylphosphonate dimer K)

26.5 mg (0.021 mmol; 1.5 eq.) of TBS-protected hydroxy-3'-succinylphosphonate dimer J were dissolved in 0.7 ml of dry dimethylformamide in a Pierce flask and treated with 6.74 mg (0.021 mmol; 1.5 eq.) of O-benzotriazol-1-yl-N,N,N',N',-tetramethyluronium tetrafluoroborate (TBTU) and 2.1 ml (0.017 mmol; 1.96 mg; 1.2 eq.) of N-ethylmorpholine. 183 mg of CPG support were then added and the mixture was shaken at room temperature for a further 4 hours. It was transferred to a frit, washed with methanol and methylene chloride, transferred to the Pierce flask again and treated with 0.7 ml of capping reagent. It was shaken for a further hour, again transferred to a frit, filtered off, washed with methanol, methylene chloride, tetrahydrofuran and diethyl ether and dried in an oil pump vacuum.

Loading of the support: 33.15 mmol/g

75. Preparation of CGTCCATGTCGGCAAACAGCT(pp)C (SEQ ID NO:37) (HSV target)

Preparation was carried out in an analogous manner to that in Example 56, starting from corresponding T(pp)T-CPG support from Example 4 instead of T(pp)T-CPG. In the condensation reactions, in step 4 the monomer building block of deoxyadenosine, deoxyguanosine or deoxycytidine corresponding to the sequence are in each case employed. Those commercially obtainable building blocks which have rapidly removable protective groups ($^R$Expedite Fast Deprotecting Amidites; Millipore, Eschborn) are preferred.

TABLE 2

| X | Nucl. | $\delta_{H\alpha}$ [ppm] | $\delta_{OH}$ [ppm] | $\delta_{C\alpha}$ [ppm] | $\delta_{31p}$ [ppm] |
|---|---|---|---|---|---|
| NMe$_2$ | d4T | — | — | — | — |
| OCH$_3$ | d4T | 4.85 | 6.64 | 69.06/68.86 (1648 Hz) (163.49 Hz) | 24.09/24.01 |
| CH$_3$ | d4T | 4.95 | 6.30 | 69.50/69.10 | 23.84/23.81 |
| H | d4T | 4.975/5.01 | 6.35 | 69.53/69.35 | 23.72/23.64 |
| Cl(MS = O.K.) | d4T | 5.05 | 6.47 | 68.47 | 23.18/23.09 |
| 2,6-diCl | d4T | 5.77 | 6.45 | — | 22.24/22.14 |
| CN | d4T | 5.19 | 6.64 | 68.99/68.90 | 22.41/22.32 |
| 4-NO$_2$ | d4T | 5.28 | 6.71 | — | 22.11/22.10 |

TABLE 2-continued

| | | | | | |
|---|---|---|---|---|---|
| 2-NO$_2$ | d4T | 6.06 | 6.83 | — | 21/72/21.65 |
| 2,4-diNO$_2$ | d4T | 7.13/7.09 | 6.13/6.11 | — | 20.21/20.46 |
| 2,6-diNO$_2$ | d4T | | | | |
| π | d4T | 5.14 | 6.605 | 69.3 | 22.24/22.13 |
| Octyl | d4T | 3.74 | 5.55 | — | 27.86/27.82 |
| NMe$_2$ | ddT | 4.885 | 6.08 | 69.2 (163.78 Hz) | 24.72/24.67 |
| OCH$_3$ | ddT | 4.98 | 6.24 | 68.83 (165.72 Hz) | 24.28/24.25 |
| CH$_3$ | ddT | 5.015 | 6.27 | 69.18 (159.06 Hz) | 24.09/24.06 |
| H | ddT | 5.056 | 6.355 | 69.33 (163.53 Hz) | 23.91/23.88 |
| Cl | ddT | 5.15 | 6.465 | 68.59 (164.016 Hz) | 23.38/23.35 |
| 2,6-diCl | ddT | 5.82 | 6.67 | 67.64 (170.2 Hz) | 22.54/22.44 |
| CN | ddT | 5.25 | 6.63 | 68.77 (166.3 Hz) | 22.65/22.60 |
| 4-NO$_2$ | ddT | 5.32 | 6.69 | 68.74 | 22.44/22.40 |
| 2-NO$_2$ | ddT | 6.07 | 6.81 | N.D. | 22.12/22.10 |
| 2,4-NO$_2$ | ddT | 6.15 | 7.07 | 69.25 | 20.77/20.61 |
| 2,6-NO$_2$ | ddT | N.D. | N.D. | N.D. | N.D. |
| π (MS O.K.) | ddT | 5.17 | 6.67 | 67.55 | 22.51/22.49 |
| Fluorenone | ddT | — | 6.75 | 80.59 (165.71 Hz) | 23.37 |
| NMe$_2$ | AZT | | | | |
| OCH$_3$ | AZT | | | | |
| CH$_3$ | AZT | | | | |
| H | AZT | | | | |
| Cl | AZT | | | | |
| CN | AZT | | | | |
| 4.NO$_2$ | AZT | 5.38 | 6.82 | — | 22.745 (DMSO) |
| 2.NO$_2$ | AZT | 6.27 | 7.31 | — | 23.17/23.08 (MeOD) |
| 2,6-NO$_2$ | AZT | 6.32 | 7.51 | — | 21.37/21.30 (MeOD) |
| 2,4-diNO$_2$ | AZT | 6.16 | 7.173 | — | 20.95/20.83 |
| (triester O.K. (MS O.K.)) | | [6.39] | [7.48] | — | [21.57/21.38] MeOD |
| π | AZT | 5.22 | 6.69 | — | 22.79/22.76 |
| Octyl (MS O.K.) | AZT | 3.83 | 5.63 | 66.72 | 28.17/28.09 |

| X | Nucleo. I | Nucleo. II | δ$_{Hα}$ [ppm] | $^{13}$C [ppm] | δ$_{OH}$ [ppm] | δ$_{31P}$ [ppm] |
|---|---|---|---|---|---|---|
| 2,6-diNO$_2$ triester O.K. | ddT | AZT | 6.34 | — | — | 21.27/21.25 (MeOD) 21.23/21.17 |
| 2,6-di-NO$_2$ triester O.K. | d4T | AZT | 6.29 | — | 7.22 | 20.38/20.28 (DMSO) 20.06/19.56 |
| 4-NO$_2$ | d4T | AZT | 5.32 | — | 6.78 | 22.63/22.20 (DMSO) |
| 2-NO$_2$ | ddT | d4T | 6.01 | — | 6.86 | 22.24/22.23/ 21.71/21.40 (DMSO) |
| 2-NO$_2$ | 3'T | d4T | 6.15 | — | 6.86 | 22.37/22.15 (DMSO) |
| 4-Cl | T | T | 5.12 | 68.36(163.20 Hz) | — | 21.5/21.01/ 23.55/23.52 (DMSO) |
| 4-Cl | T$_{3'heo}$ | T$_{3'heo}$ | 5.16 | 68.38 (163.30 Hz) | 6.58 | 23.68/23.66 (DMSO) |
| 4-Cl | T$_{3'TBDMS}$ | T$_{3'TBDMS}$ | 5.12 | 68.32 (163 Hz) | N.D. | 23.25/22.86 (CDCl$_3$) |
| 4-Cl | T$_{3'Ac}$ | T$_{3'Ac}$ | 5.16 | 68.49 (164.05 Hz) | 6.59 | 23.77/23.73 (DMSO) |
| 4-OCH$_3$ | T$_{3'Ac}$ | T$_{3'Ac}$ | 5.05 | 68.72 (165.12 Hz) | 6.38 | 24.59/24.52 (DMSO) |

| H-Phosphonate diester and H-phosphonate monoester | | | | | |
|---|---|---|---|---|---|
| Nucl. 1 | Nucl. II | δ$_H$ [ppm] | J$_{HP}$ [Hz] | δ$_{31P}$ [ppm] | LM |
| ddT | ddT | 6.949 | 711.00 | 11.18 | DMSO |
| ddT | — | 6.815 | 637.01 | 7.24 | D$_2$O |
| d4T | d4T | 6.87 | 710.98 | 11.12 | DMSO |
| d4T | — | 6.71 | 637.67 | 7.07 | D$_2$O |
| AZT | AZT | 6.97 | 719.4 | 11.40 | DMSO |
| AZT | — | 7.02 | 674.54 | 1.06 | DMSO |
| ddT | d4T | 6.91 | 711.10 | 11.35/10.88 | DMSO |
| ddT | AZT | 6.939 | 736.51 | 11.35/11.26 | DMSO |
| d4T | AZT | 6.954 | 739.59 | 11.46/11.09 | DMSO |
| $^3$'T | AZT | 7.026 | 720.12 | 10.51/10.04 | DMSO |
| $^3$'T | d4T | 6.97 | 716.55 | 10.15/10.07 | DMSO |

I claim:
1. Compounds of the formula I,

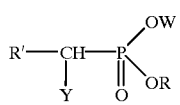
(I)

wherein
Y is OH, SH, OAc or SAc, where Ac is a (C1–C18)-acyl, which is saturated or 1–3 times unsaturated,
R' is aryl having 6 to 14 carbon atoms, heteroaryl having 3 to 13 carbon atoms and up to 3 heteroatoms selected from the group consisting of N, O and S, or alkyl,
W is 5'-, 3' or 2' nucleoside analogue of a steroid, sugar, inositol, or peptide having at least one amino acid Ser or Tyr and a total of up to 20 natural amino acids,
R has the meaning of W, where R and W can be identical or different, or R is an alkyl radical that is substituted or unsubstituted, or
W and R, together with the phosphonate radical carrying them, form an oligonucleotide where W is a radical of the formula II and R is a radical of the formula II'

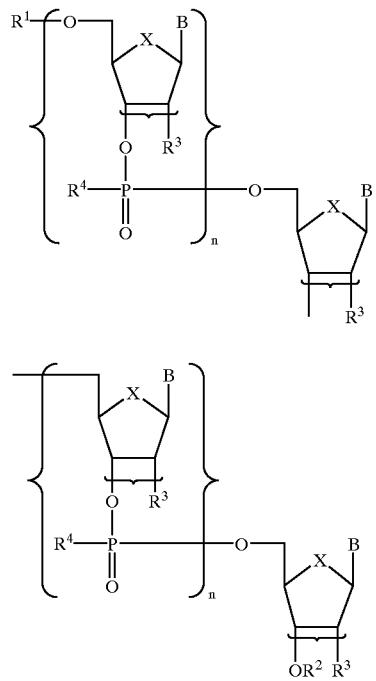
(II)

(II')

where
X is oxy, sulphanediyl or methylene,
B independently of one another is a nucleotide base, n independently of one another is an integer from 0 to 50, $R^1$ and $R^2$ independently of one another are H, (C1–C18) acyl or a radical of the formula

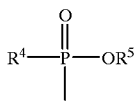

in which
$R^4$ is $O^-$, $S^-$, $CH_3$ or CHYR', where R' and Y are as defined above and $R^5$ is an alkyl radical that is substituted or unsubstituted having 1–18 carbon atoms,
$R^3$ is independently of one another H, O(C1–C18)-alkyl, O(C1–C18)-acyl, F, Cl, $N_3$, $NH_2$ or $NHR^6$ where $R^6$ is (C1–C6)-alkyl or -acyl and the curved bracket indicates that $R^3$ and the adjacent phosphonyl radical can be in the 2' or 3' position.

2. Compounds of the formula I according to claim 1, wherein
Y is OH, SH, OAc or SAc, where Ac is a (C1–C8)-acyl, which is saturated or unsaturated 1–3 times,
R' is an aryl having 6–14 carbon atoms that is unsubstituted or substituted by up to three radicals which are independent of one another, selected from the group consisting of (C1–C5)-alkyl, halogen, $NO_2$, CN, (C1–C6)-alkoxy, amino, (C1–C4)-alkylamino, (C1–C8)-dialkylamino, where a (C3–C8)-alkylene radical in which a $CH_2$ group can also be replaced by oxy can also be fused on to the aryl radical;
a heteroaryl having 3 to 13 carbon atoms and up to 3 heteroatoms selected from the group consisting of N, O and S; or
a (C1–C16)-alkyl, which is branched or unbranched, saturated or unsaturated 1–3 times, unsubstituted or substituted independently of one another by up to three substituents selected from the group consisting of halogen, CN, $NO_2$ and (C1–C3)-alkoxy,
W is a pharmaceutical active compound radical,
R has the meaning of W, where R and W can be identical or different, or R is a (C1–C16)-alkyl, which can be branched or unbranched and is unsubstituted or substituted independently of one another by up to 3 radicals from the group consisting of halogen, CN, (C1–C8)-acyloxy, (C1–C18)-alkoxy or W and R, together with the phosphonate radical carrying them, form an oligonucleotide where W is a radical of the formula II and R is a radical of the formula II' where
X is oxy or sulphanediyl,
B independently of one another is a nucleotide base,
n independently of one another is an integer from 0 to 30,
$R^1$ and $R^2$ independently of one another are H(C1–C12)-acyl or a radical of the formula

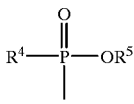

in which
R⁴ is O, S, CH₃ or CHYR', where R' and Y are as defined above and R⁵ is an unsubstituted or substituted alkyl radical having 1–12 carbon atoms,
R³ independently of one another is H, O(C1–C12)-alkyl, O(C1–C12)-acyl, Cl, N₃, NH₂ or NHR⁶ where R⁶ is (C1–C3)-alkyl or -acyl,
and the curved bracket indicates that R³ and the adjacent phosphonyl radical can be in the 2' or 3' position.

3. Compounds of the formula I according to claims 1, wherein
Y is OH, SH, OAc or SAc, where Ac is a (C1–C3)-acyl, which is saturated or unsaturated 1–3 times,
R' is an aryl having 6–14 carbon atoms, that is unsubstituted or substituted by up to 3 radicals which are independent of one another, selected from the group consisting of (C1–C3)-alkyl, F, Cl, NO₂, CN, (C1–C4)-alkoxy, amino, (C1–C3)-alkylamino, (C1–C6)-dialkylamino, where a (C3–C8)-alkylene radical in which a CH₂ group can also be replaced by oxy can also be fused onto the aryl radical;
a heteroaryl having 3 to 6 carbon atoms and up to 3 heteroatoms selected from the group consisting of N, O and S; or
a (C1–C8)-alkyl, which is branched or unbranched, saturated or unsaturated 1–3 times, unsubstituted or substituted independently of one another by up to three substituents selected from the group consisting of Cl, CN, NO₂ and (C1–C3)-alkoxy,
W has the meaning of a 5'-, 3' or 2' nucleoside analogue of a steroid, sugar, inositol, or peptide having at least one amino acid Ser or Tyr and a total of up to 20 natural amino acids,
R has the meaning of W or is (C1–C8)-alkyl, which can be branched or unbranched and is unsubstituted or substituted by up to 2 radicals from the group consisting of halogen, CN (C3–C6)-acyloxy, (C8–C18)-alkoxy, or
W and R, together with the phosphonate radical carrying them, form an oligonucleotide where W is a radical of the formula II and r is a radical of the formula II' where X is oxy,
B independently of one another is a nucleotide base,
n independently of one another is an integer from 0 to 20,
R¹ and R² independently of one another are H (C1–C8)-acyl or a radical of the formula

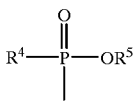

in which
R⁴ is O, S, CH₃ or CHYR', where R' and Y are as defined above and R⁵ is an unsubstituted or substituted alkyl radical having 1–8 carbon atoms,
R³ independently of one another is H, O(C1–C8)-alkyl, O(C1–C8)-acyl, Cl or N₃, and the curved bracket indicates that R₃ and the adjacent phosphonyl radical can be in the 2' or 3' position.

4. Compounds of the formula I according to claim 1, wherein
Y is OH,
R' is an aryl having 6 carbon atoms, unsubstituted or substituted by up to 3 radicals which are independent of one another, selected from the group consisting of (C1–C3)-alkyl, F, Cl, NO₂, CN, (C1–C4)-alkoxy, amino, (C1–C3)-alkylamino, (C1–C6)-dialkylamino, where a (C3–C6)-alkylene radical in which a CH₂ group can also be replaced by oxy can also be fused onto the aryl radical;
a heteroaryl having 3 to 6 carbon atoms and up to 3 heteroatoms selected from the group consisting of N, O and S; or
a (C1–C8)-alkyl, which is branched or unbranched, saturated or unsaturated 1–3 times, unsubstituted or substituted independently of one another by up to three substituents selected from the group consisting of Cl, CN, NO₂ and (C1–C3)-alkoxy;
W has the meaning of a 5'- or 3' nucleoside analogue,
R has the meaning of W or is a (C1–C4)-alkyl, which can be branched or unbranched or
W and R, together with the phosphonate radical carrying them, form an oligonucleotide where W is a radical of the formula II and R is a radical of the formula II' where X is oxy,
B independently of one another is a nucleotide base,
n independently of one another is an integer from 0 to 15,
R¹ and R² independently of one another are H (C1–C4)-acyl or a radical of the formula

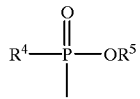

in which
R⁴ is O, S, CH₂ or CHYR', where R' and Y are as defined above and R⁵ is an unsubstituted or substituted alkyl radical having 1–3 carbon atoms,
R³ independently of one another is H, O(C1–C3)-alkyl, O(C1–C3)-acyl, Cl or N₃, and the curved bracket indicates that R³ and the adjacent phosphonyl radical can be in the 2' or 3' position.

5. Compounds of the formula I according to claim 4, wherein R' is a (C1–C8)-alkyl, which is unsaturated in conjugated form having an unsaturated bond in the alpha-position, branched or unbranched, unsubstituted or substituted independently of one another by up to three substituents selected from the group consisting of Cl, CN, NO₂ and (C1–C3)-alkoxy.

6. Compounds of the formula I according to claim 1, wherein
Y is OH,
W has the meaning of a 5'- or 3' nucleoside analogue,
R has the meaning of W or is a (C1–C4)-alkyl, which can be branched or unbranched,
R' is aryl having 6 carbon atoms, unsubstituted or substituted by up to 3 radicals which are independent of one another, selected from the group consisting of Cl, NO₂, CH, (C1–C3)-alkoxy, amino and (C1–C3)-alkylamino.

7. A process for the preparation of compounds according to claims 1, comprising, a) reacting a compound of the formula III with a compound of the formula IV,

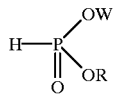
(III)

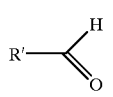
(IV)

or b) reacting a compound of the formula V with compounds of the formula VI in any desired sequence and using a condensing agent, or c) reacting a compound of the formula V with compounds of the formula VI and of the formula VII in any desired sequence and using a condensing agent,

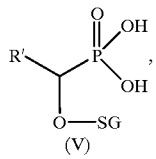  , WOH,   ROH, (V)    (VI)    (VII)

where SG is a protective group which can be removed to obtain the compound of the formula I, or a nucleotide unit having a 3'(2')-terminal H-phosphonate group and the protected 5'-hydroxy group is reacted with a further nucleotide unit having a free 5'-hydroxy group and protected 3' (2')-hydroxy group in the presence of an activating agent to give the H-phosphonate dinucleoside and this is condensed with an aldehyde to give the dinucleoside α-hydroxy-alkyl (aryl)phosphonate, which after reaction to give its activated derivatives reacts which further (oligo)nucleotide fragments to give oligonucleotides with temporarily introduced protective groups being removed, or d) a nucleotide unit having a 3'(2')-terminal phosphorus (III) or phosphorus(V) group is reacted with a free 5'-hydroxy group of a further nucleotide unit or growing oligonucleotide chain in the presence of a condensing agent, or e) the oligonucleotide analogue or its activated derivatives is built up in fragments in the same way, with protective groups temporarily introduced into the oligonucleotides obtained according to a) or b) for the protection of other functions are removed and the oligonucleotide analogues of the formula I are thus obtained in which W is a radical of the formula II and R is a radical of the formula II' are optionally converted into their physiologically tolerable salt.

8. A method of inhibiting gene expression comprising contacting DNA of a gene with the oligonucleotide analogue according to claim 1 to inhibit expression of said gene.

9. A pharmaceuticals composition comprising one or more of the compounds of the formula I according to claim 1 and a pharmaceutically acceptable carrier.

10. A method of treating a host comprising administering to said host a pharmaceutical composition as claimed in claim 9.

11. The method of claim 10, wherein said pharmaceutical composition has a prodrug function.

* * * * *

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

ACACCCAATT CTGAAAATGG                                         20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

AGGTCCCTGT TCGGGCGCCA                                         20

(2) INFORMATION FOR SEQ ID NO:3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GTCGACACCC AATTCTGAAA ATGGATAA                                28

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GCTATGTCGA CACCCAATTC TGAAA                                   25

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
TCGTCGCTGT CTCCGCTTCT TCTTCCTGCC A                                              31

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GCGGGGCTCC ATGGGGGTCG                                                           20

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CAGCTGCAAC CCAGC                                                                15

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GGCTGCTGGA GCGGGGCACA C                                                         21

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

AACGTTGAGG GGCAT                                                                15

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GTGCCGGGGT CTTCGGGC                                                             18
```

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GGAGAACATC ATGGTCGAAA G                                              21

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CCCGAGAACA TCATGGTCGA AG                                             22

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GGGGAAAGCC CGGCAAGGGG                                                20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CACCCGCCTT GGCCTCCCAC                                                20

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GGGACTCCGG CGCAGCGC                                                  18

(2) INFORMATION FOR SEQ ID NO:16:

(i) SEQUENCE CHARACTERISTICS:
        (A) LENGTH: 20 base pairs (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:16:

GGCAAACTTT CTTTTCCTCC                                        20

(2) INFORMATION FOR SEQ ID NO:17:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:17:

GGGAAGGAGG AGGATGAGG                                         19

(2) INFORMATION FOR SEQ ID NO:18:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:18:

GGCAGTCATC CAGCTTCGGA G                                      21

(2) INFORMATION FOR SEQ ID NO:19:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:19:

GCAGTAAGCA TCCATATC                                          18

(2) INFORMATION FOR SEQ ID NO:20:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:20:

CCCCCACCAC TTCCCCTCTC                                        20

(2) INFORMATION FOR SEQ ID NO:21:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:21:

CTCCCCCACC ACTTCCCCTC                                               20

(2) INFORMATION FOR SEQ ID NO:22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GCTGGGAGCC ATAGCGAGG                                                19

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

ACTGCTGCCT CTTGTCTCAG G                                             21

(2) INFORMATION FOR SEQ ID NO:24:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CAATCAATGA CTTCAAGAGT TC                                            22

(2) INFORMATION FOR SEQ ID NO:25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

GTGTCGGGGT CTCCGGGC                                                 18

(2) INFORMATION FOR SEQ ID NO:26:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

```
CACGTTGAGG GGCAT                                                          15

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

GTCTTCCATA GTTACTCA                                                       18

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

GATCAGGCGT GCCTCAAA                                                       18

(2) INFORMATION FOR SEQ ID NO:29:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 9..10
        (D) OTHER INFORMATION: /note= "NN at the 9 and 10
            positions is defined as two thymine bonded by an alpha-
            hydroxy (o-nitrophenyl) methylphosphonate bridge."

(xi) SEQUENCE DESCRIPTION: SEQ ID NO:29:

TTTTTTTTNN                                                                10

(2) INFORMATION FOR SEQ ID NO:30:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..2
        (D) OTHER INFORMATION: /note= "NN at the 1 and 2 positions
            is defined as two thymine bonded by an alpha-hydroxy
            (o-nitrophenyl) methylphosphonate bridge."

(xi) SEQUENCE DESCRIPTION: SEQ ID NO:30:

NNTTTTTTTT                                                                10

(2) INFORMATION FOR SEQ ID NO:31:
```

```
    (i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: one-of(1, 2, 9, 10)
        (D) OTHER INFORMATION: /note= "NN at the 1/2 and 9/10
            positions are defined as two thymine bonded by an
            alpha-hydroxy (o-nitrophenyl) methyphosphonate bridge."

(xi) SEQUENCE DESCRIPTION: SEQ ID NO:31:

NNTTTTTTNN                                                              10

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 20..21
        (D) OTHER INFORMATION: /note= "NN at the 20 and 21 position
            is defined as a guanine at the 20 position bonded to a
            cytosine at the 21 position by an alpha-hydroxy
            (o-nitrophenyl) methylphosphonate bridge."

(xi) SEQUENCE DESCRIPTION: SEQ ID NO:32:

GCAGGAGGAT GCTGAGGAGN N                                                 21

(2) INFORMATION FOR SEQ ID NO:33:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: one-of(1, 2, 20, 21)
        (D) OTHER INFORMATION: /note= "NN at the 1/2 and 20/21
            positions are defined as a guanine at the 1 and 20
            position bonded to a cytosine at the 2 and 21 positions,
            respectively, by an alpha-hydroxy (o-nitrophenyl)
            methylphosphonate bridge."

(xi) SEQUENCE DESCRIPTION: SEQ ID NO:33:

NNAGGAGGAT GCTGAGGAGN N                                                 21

(2) INFORMATION FOR SEQ ID NO:34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
```

(B) LOCATION: one-of(1, 2, 11, 12, 20, 21)
            (D) OTHER INFORMATION: /note= "NN at the 1/2, 11/12, 20/21
                positions are defined as a guanine at the 1, 11, and 20
                positions bonded to a cytosine at the 2, 12, and 21
                positions, respectively, by an alpha-hydroxy
                (o-nitrophenyl) methylphosphonate bridge."

(xi) SEQUENCE DESCRIPTION: SEQ ID NO:34:

NNAGGAGGAT NNTGAGGAGN N                                                    21

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: one-of(1, 2, 19, 20)
        (D) OTHER INFORMATION: /note= "NN at the 1/2 position is
            defined as a guanine at the 1 position bonded to a
            cytosine at the 2 position by an alpha-hydroxy
            (o-nitrophenyl) methyl phosphonate bridge. NN at the
            19/20 position is defined as a cytosine at the 19
            position bonded to a guanine at the 20 position by an
            alpha-hydroxy (o-nitrophenyl), methylphosphonate bridge."

(xi) SEQUENCE DESCRIPTION: SEQ ID NO:35:

NNGGGGCTCC ATGGGGGTNN                                                      20

(2) INFORMATION FOR SEQ ID NO:36:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: one-of(1, 2, 16, 17)
        (D) OTHER INFORMATION: /note= "NN at the 1/2 and 16/18
            positions are defined as a cytosine, at the 1 and 16
            positions bonded to a guanine at the 2 and 17 positions,
            respectively, by an alpha-hydroxy (o-nitrophenyl)
            methylphosphonate bridge."

(xi) SEQUENCE DESCRIPTION: SEQ ID NO:36:

NNAGAACATC ATGGTNN                                                         17

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: one-of(21, 22)
        (D) OTHER INFORMATION: /note= "NN at the 21/22 position is
            defined as a thymine at the 21 position bonded to a -continued cytosine at the 22 position by an alpha-hydroxy
(o-nitrophenyl) methylphosphonate bridge."

(xi) SEQUENCE DESCRIPTION: SEQ ID NO:37:

CGTCCATGTC GGCAAACAGC NN                       22